United States Patent
Takeda et al.

(10) Patent No.: US 9,423,329 B2
(45) Date of Patent: Aug. 23, 2016

(54) TESTING APPARATUS

(71) Applicants: Hitachi, Ltd., Tokyo (JP); Shimadzu Corporation, Kyoto (JP)

(72) Inventors: Norio Takeda, Tokyo (JP); Shohei Watanabe, Kyoto (JP); Tadaoki Takii, Kyoto (JP)

(73) Assignees: Hitachi, Ltd, Tokyo (JP); Shimadzu Corporation, Kyoto (JP)

( * ) Notice: Subject to any disclaimer, the term of this patent is extended or adjusted under 35 U.S.C. 154(b) by 0 days.

(21) Appl. No.: 14/625,800

(22) Filed: Feb. 19, 2015

(65) Prior Publication Data
US 2015/0253227 A1    Sep. 10, 2015

(30) Foreign Application Priority Data

Mar. 7, 2014    (JP) .................................. 2014-045523

(51) Int. Cl.
*G01N 3/08*    (2006.01)

(52) U.S. Cl.
CPC ......... *G01N 3/08* (2013.01); *G01N 2203/0016* (2013.01); *G01N 2203/0017* (2013.01);
(Continued)

(58) Field of Classification Search
CPC ............. G01N 2203/0252; G01N 2203/0254; G01N 2203/0256; G01N 2203/0016; G01N 2203/0017; G01N 2203/0073; G01N 2203/0085
USPC .......... 73/788, 794–798, 818–819, 825, 826, 73/831, 833, 837, 856, 857, 860, 73/862.041–862.045
See application file for complete search history.

(56) References Cited

U.S. PATENT DOCUMENTS

| | | | | |
|---|---|---|---|---|
| 3,315,301 | A * | 4/1967 | Dibblee | B29C 55/04 26/1 |
| 4,677,854 | A * | 7/1987 | Gabelli | B29C 55/10 73/794 |

(Continued)

FOREIGN PATENT DOCUMENTS

| | | |
|---|---|---|
| JP | 2007-510151 | 4/2007 |
| JP | 2012-202974 | 10/2012 |
| WO | 2005/040765 | 5/2005 |

OTHER PUBLICATIONS

Masao Sakane et al., High Temperature Biaxial Low Cycle Fatigue Using Cruciform Specimen, The Society of Materials Science, vol. 37, No. 414, pp. 340-346, 1988.

(Continued)

*Primary Examiner* — Lisa Caputo
*Assistant Examiner* — Jonathan Dunlap
(74) *Attorney, Agent, or Firm* — Mattingly & Malur, PC

(57) ABSTRACT

A strength testing apparatus has a plurality of testing axes, each of which breaks a test piece in a central area thereof. The apparatus has a plurality of 1-axis testing structures each having: an actuator, which is configured to move linearly, thereby to apply a load onto a test body; an actuator fixing base, which is configured to fix the actuator at a predetermined position; a reaction base comprising a chucking tool, which is configured to chuck a test piece, in a chucking tool, which is provided at an end portion of the actuator; and a base, which is configured to connect the actuator fixing base and the reaction base, wherein all of the testing axes, each almost passing through an axial center of each actuator, come across at one (1) point, and the 1-axis testing structures are arranged so that they are included in a same plane.

5 Claims, 20 Drawing Sheets

(52) U.S. Cl.
CPC ............. *G01N2203/0073* (2013.01); *G01N 2203/0085* (2013.01); *G01N 2203/0252* (2013.01); *G01N 2203/0254* (2013.01); *G01N 2203/0256* (2013.01)

(56) References Cited

U.S. PATENT DOCUMENTS

| | | | | |
|---|---|---|---|---|
| 5,552,006 | A * | 9/1996 | Soliday | B29C 55/10 156/108 |
| 5,680,262 | A * | 10/1997 | Soliday | B29C 55/10 359/840 |
| 6,860,156 | B1 * | 3/2005 | Cavallaro | G01N 3/08 73/813 |
| 7,204,160 | B1 * | 4/2007 | Sadegh | G01N 3/10 73/862.041 |
| 7,509,882 | B2 | 3/2009 | Monteiro et al. | |
| 7,712,379 | B2 * | 5/2010 | Abu-Farha | G01N 3/04 73/856 |
| 7,762,146 | B2 * | 7/2010 | Brodland | G01N 3/04 73/826 |
| 7,785,517 | B2 * | 8/2010 | Poe | C08G 73/10 248/576 |
| 8,342,492 | B2 * | 1/2013 | Poe | F16F 15/04 248/200 |
| 2008/0034885 | A1 * | 2/2008 | Monteiro | G01N 3/08 73/794 |

OTHER PUBLICATIONS

Extended European Search Report received in corresponding European Application No. 16155632.1 dated Sep. 10, 2015.

Urumov, G. T., "A Machine for Testing Sheet Specimens for Fatigue Under Two-Frequency Loading Conditions", Industrial Laboratory (Diagnostics of Materials), Oct. 1997, pp. 620-622, vol. 63, No. 10, New York.

Boehler, J. P. et al., "A New Direct Biaxial Testing Machine for Anisotropic Materials", Experimental Mechanics, Mar. 1994, pp. 1-9, vol. 34, No. 1, New York.

\* cited by examiner

TESTING APPARATUS

BACKGROUND OF THE INVENTION

The present invention relates to a testing apparatus of strength.

A complex loads acts, repetitively, upon the transportation equipment, such as, a vehicle or a railway, etc., construction machinery, such as, a power shovel or a dump truck, etc., and/or the structure system of a natural energy power generating system, such as, for the wind-power generation or the wave-power generation, when operating, because of the various reasons thereof. This complex repetitive load is so-called a multi-axes repetitive load, changing amplitude in the waveform of the load with an elapse of time, as well as, changing a direction of the load, and may cause fatigue failure on such machines, as was mentioned above. For the purpose of avoiding such fatigue failure therefrom, it is important to fully understand a phenomenon of the fatigue to the multi-axes repetitive load. For such purpose as was mentioned above, multi-axes strength testing machines are invented and/or developed, for enabling a fatigue test on the multi-axes repetitive load.

The most general multi-axes strength testing machine is an apparatus having the structure, i.e., applying two (2) axes loads, such as, an axial direction load (e.g., a tensile/compressive load) and a torsion load, upon one end of a test piece having a rod-like or cylinder-like shape, while hold the other end thereof fixedly. Comparing to the other multi-axes strength testing machines having two (2) or more pieces of testing axes, which will be mentioned later, this type of multi-axes strength testing machine has only one (1) piece of a testing axis. This type of multi-axes strength testing machine has two (2) sets of actuators, such as, a translatory movement actuator to be used for the load in the axial direction, and rotary actuator to be used for the torsion load. Changing a waveform of the load in the axial direction and also a phase of a waveform of the torsion load enables a test under the multi-axes load (this will be called "non-proportional load"), i.e., chaining the direction of a main stress of the multi-axes stress generating on the test piece with an elapse of time. However, with this type of multi-axes strength testing machine, a condition of the multi-axes stress, which can achieved on the test piece, is limited. In more details, with this type of the apparatus, only a test is possible, under the condition of multi-axes stress where a ratio of main stress $\lambda = \sigma 3/\sigma 1$ obtained falls within a range of $-1 \leq \lambda \leq 0$, where $\sigma 1$ is the maximum main stress and $\sigma 3$ is the minimum main stress.

For the purpose of implementing a test exceeding the range of this main stress ratio is developed a multi-axes testing apparatus, having such structure as is written in the following Non-Patent Document 1. In this apparatus are disposed four (4) sets of translatory actuators, in a total thereof, each being so arranged to apply a load, respectively, to four (4) pieces of end portions of a cross, with respect to a test piece having almost cross-like shape. Two (2) sets of actuators are disposed so as to face to each other, thereby forming a 1-axis test structure, and two (2) sets of the 1-axis test structures enable the multi-axes fatigue test for the 2-axes load. The testing axis, passing through a center of the axes of the two (2) sets of the actuators facing to each other, comes across the axis of the other testing axis, which is constructed with other pair of actuators, at one point, and this point is coincident with a center of the test piece. With controlling the load applied by means of each actuator, it is possible to generate the condition of multi-stress condition at a central area of the test piece, including the center of the test piece therein. With is apparatus, it is possible to implement the test under the multi-stress condition mentioned above, i.e., within the range of the main stress $-1 \leq \lambda \leq 0$, however, in relation with such non-proportional load, as was mentioned above, only a part of the non-proportional load can be made. Also, because the two (2) sets of actuator build up the 1-axis test structure, there is a necessity of controlling the actuators facing to each other, at high accuracy, for maintaining the center of the test piece at the crossing point of the testing axes.

In the following Patent Document 1 is disclosed an apparatus, including three (3) or more sets of the 1-axis test structures, each for use of a mechanical load, and comprising a magnetic characteristic measurement means for a magnetic material. With this apparatus, it is possible to estimate the magnetic characteristic of the magnetic material under an arbitrary multi-stress condition. The testing axes, staying by three (3) or more pieces corresponding to the three (3) or more sets of the 1-axis test structures, cross one another at one (1) point, and the cross point thereof lies within a central area of the test piece. By means of a stress applying means, it is possible to generate the multi-stress condition within the central area of the test piece. With such structure of that apparatus, as is shown in this patent, it is possible to achieve the multi-stress condition within the range, where the main stress ratio lies in the range $-1 \leq \lambda \leq 0$, and also to direct the main stress of the multi-stresses into an arbitrary direction. The test piece has a shape or configuration, extending end portions thereof, radially, from the center of the test piece, fitting to the number of the testing axes and the directions of the axes. As an embodiment of the Patent Document is shown the structure of the apparatus, which provides a load means (e.g., a weight or a hydraulic actuator) so as to act a tensile load and a compressive load upon the end portion of the test piece. This means that those two (2) sets of the actuators build up the 1-axis test structure, similar to that show in the Non-Patent Document 1.

In the following Patent Document 2 is disclosed a multi-axes universal testing apparatus, comprising plural numbers of 1-axis test structures, similar to that show in the Patent Document 1. The apparatus is so constructed that the testing axes, being provided by the number same to that of those 1-axis test structures, cross a certain one (1) point. Since electromotive actuators are provided on both ends of each axis, this apparatus has the structures, being same to that shown in the Non-Patent Document 1, judging from a viewpoint that the two (2) sets of actuators build up the 1-axis test structure. This apparatus, similar to that show in the Patent Document 1, is able to achieve the multi-stress condition within the range of $-1 \leq \lambda \leq 0$, in the main stress ratio, and also to direct the main stress of the multi-axes stresses into an arbitrary direction.

PRIOR ART DOCUMENTS

Patent Documents

[Patent Document 1] Japanese Patent Laying-Open No. 2012-202974 (2012); and
[Patent Document 2] Japanese Patent Laying-Open No. 2007-510151 (2007).

Non-Patent Documents

[Non-Patent Document 1] "High Temperature Biaxial Low Cycle Fatigue Using Cruciform Specimen", Material, Volume 37, No. 414, pp 340-346, 1988.

BRIEF SUMMARY OF THE INVENTION

In case of building up the apparatus to have two (2) or more pieces of testing axes, and wherein those testing axes cross at a certain one (1) point, the central area or region of the test piece is disposed at the cross point of those testing axes, so as to generate the multi-axes stress condition within that central area. Accordingly, it is necessity to hold the test piece on the apparatus, fixedly, and to apply the load thereon. In the testing apparatuses, which are described in the Non-Patent Document 1, and the Patent Documents 1 and 2, two (2) sets of stress loading apparatuses (e.g., actuators, etc.) are disposed to face to each other, thereby to obtain the 1-axis test structure. In case of applying such the structure, i.e., the 1-axis test structure, a positional shift is generated at the cross point between the central area of the test piece and the testing axis, when a balance is broken between the loads of the stress loading apparatuses facing to each other. In case of aiming to generate the multi-axes stress condition, as is in the Patent Document 1, a certain level of the positional shift between the central area of the test piece and the cross point of the testing axes does not matter. However, in order to analyze the fatigue phenomenon due to the multi-axes stresses, it is needed to generate the multi-axes stresses, repetitively, at the central area of the test piece, thereby generating the fatigue failure in the central area of the test piece. In case of the test piece, having the configuration extending the end portions, radially, from the center of the test piece (i.e., the cross-like shape in case of two (2) axes of the testing axes), a bending load or stress acts on an arm portion when the positional shift is generated between the central area of the test piece and the cross point of the testing axes, if calling a portion, extending from the end portion, at which the test piece is chucked on the apparatus, to the center thereof, the "arm portion". With this bending load or stress, there is a possibility of generating the fatigue failure at a joint of the arm, before the fatigue failure is generated in the central area of the test piece. For avoiding such fatigue failure therefrom, generating at an undesirable portion of the test piece, in the testing apparatuses, which are described in the Non-Patent Document 1, and the Patent Documents 1 and 2, it is necessary to control the loads of the stress loading apparatuses facing to each other, restrictively, so that the cross point of the testing axes is included, always, within the central area of the test piece.

Also, essentially, for the purpose of achieving a testing structure of one (1) axis, it is sufficient to apply such structure of an apparatus, while fixing an end of the test piece, such as, having a sandglass-shape or a dumbbell-shape, applying the load on the other end thereof. In other words, it is enough to provide one (1) set of the stress loading apparatus, at the least, for building up the 1-axis test structure. On the contrary to this, in each of the apparatuses, which are described in the Non-Patent Document 1, and the Patent Documents 1 and 2, are includes two (2) sets of the stress loading apparatuses in the 1-axis test structure thereof, then the apparatus comes to be high in the prices thereof if the number of the testing axes increases up.

According to the present invention, being accomplished by taking such the problems into the consideration thereof, and in the details thereof, an object thereof is to provide a testing apparatus for the strength, having plural numbers of testing axes therein, to be less in the number of the stress loading apparatuses and low in the prices thereof, and also automatically adjusting the cross point of the testing axes to the central area of the test piece during when the test is conducted.

According to the present invention, for dissolving such problems as mentioned above, there is applied the structure, which will be described later, in the pending claims, for example. According to the present invention, though including plural numbers of means for dissolving the problems mentioned above, and if listing up one example of them, there is provided 1. A testing apparatus, including a plural number of 1-axis testing structures therein, the each 1-axis testing structure comprising: an actuator, which is configured to move linearly, thereby to apply a load onto a test body; an actuator fixing base, which is configured to fix said actuator at a predetermined position; a reaction base comprising a chucking tool, which is configured to chuck a test piece, in a pair of other chucking tool, which is provided at end portion of said actuator; and a base, which is configured to connect said actuator fixing base and said reaction base, wherein all of testing axes, each almost passing through an axial center of the each actuator, come across at one (1) point, and said 1-axis testing structures are arranged so that they are included in a same plane.

Also, for the purpose of disposing the testing axis in the central area of the test piece, automatically, when testing, so as to generate the fatigue failure from the central area of the test piece, the each 1-axis testing structure is able to move in parallel with a plane including all of the testing axes, each almost passing through the axial center of the each actuator, or is fixed at a position thereof, and under a condition that the test piece is not attached, the movable 1-axis testing structure is not prevented from moving by other 1-axis testing structure.

Effect(s) of the Invention

According to the present invention, since the stress loading apparatus included in the 1-axis testing structure is only one (1) set, a number of the actuators necessary is three (3), even if preparing three (3) sets of the 1-axis testing structures, and for this reason, it is possible to provide the multi-axes strength testing apparatus, which is low in the price thereof and enables the test with stability.

Those and other objects, features and advantages of the present invention will become more readily apparent from the following detailed description when taken in conjunction with the accompanying drawings below.

DETAILED DESCRIPTION OF THE PREFERRED EMBODIMENTS

Figure 1:
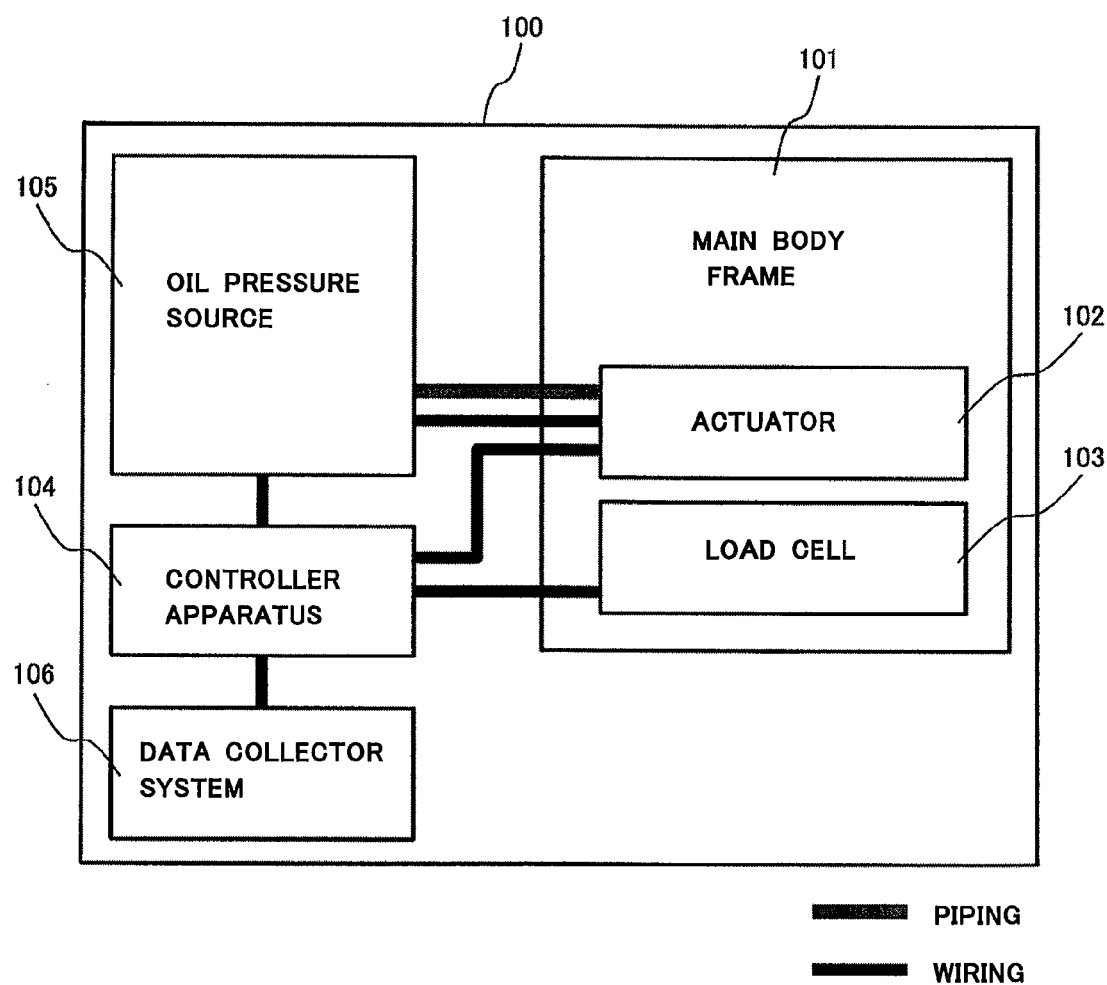
FIG. 1 is a block diagram for showing the entire of a strength testing apparatus, according to the present invention.

Hereinafter, embodiments according to the present invention will be fully explained by referring to the attached drawings.

First of all, explanation will be given on the entire structures of a strength testing apparatus 100, which are in common with the embodiments of the present invention. On a main body frame 101 are attached an actuator 102, for applying a load on a test piece, and a load cell 103, for detecting the load thereon. The main body frame 101 has a structure, being sufficiently hard or rigid with respect to the load that the actuator 102 generates, so as to hold the actuator 102 and the load cell 103 at a certain position during the time of testing. The actuator 102 and the load cell 103 are disposed on the main body frame 101, by plural numbers of pairs thereof, depending on the number of testing axes. To the actuator 102 is applied a translatory actuator, a movable part of which translates. In case where the actuator 102 is driven by an oil pressure, an oil pressure source 105 may be included within the strength testing apparatus 100. However, the strength testing apparatus 100 according to the present invention may be built up with, not only such hydraulically operated actuator, but also with an electromotive actuator or other stress loading apparatuses, etc. The actuator 102 is controlled on a load or an amount of translatory stroke, by a controller apparatus 104. The controller apparatus 104 conducts a feedback control, while observing an output of other detector (e.g., a displacement sensor, etc.) not shown in the figure, so that the actuator 102 can generate a predetermined load or an amount of stroke. There may be a case of applying plural numbers of the controller apparatuses 104, being same to the number of the actuators 102, or in other case, a controller apparatus 104 is applied, which can control the plural numbers of the actuators 102, at the same time. A data collector system 105 is a system for recording the load and the stroke amount, etc., which are observed and/or controlled by the controller apparatus 104, and for example, to that may be applied a PC (personal computer) or the like. In case where the output of the detector not shown in the figure be observed/controlled by the controller apparatus 104, that output can be recorded into the data collector system 105.

<Embodiment 1>

Figure 2:
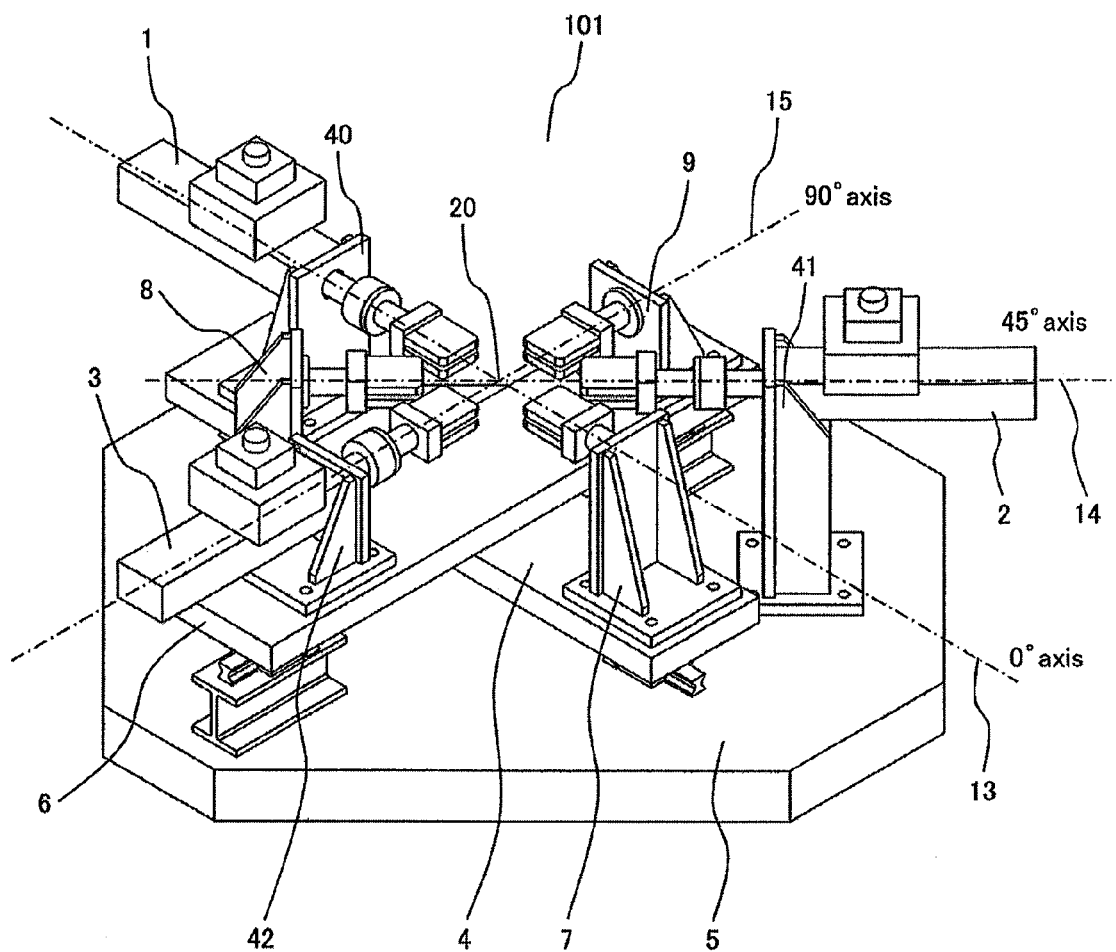
FIG. 2 is a perspective view for showing a first example of the structure of the strength testing apparatus, according to a first embodiment of the present invention.
Figure 3:
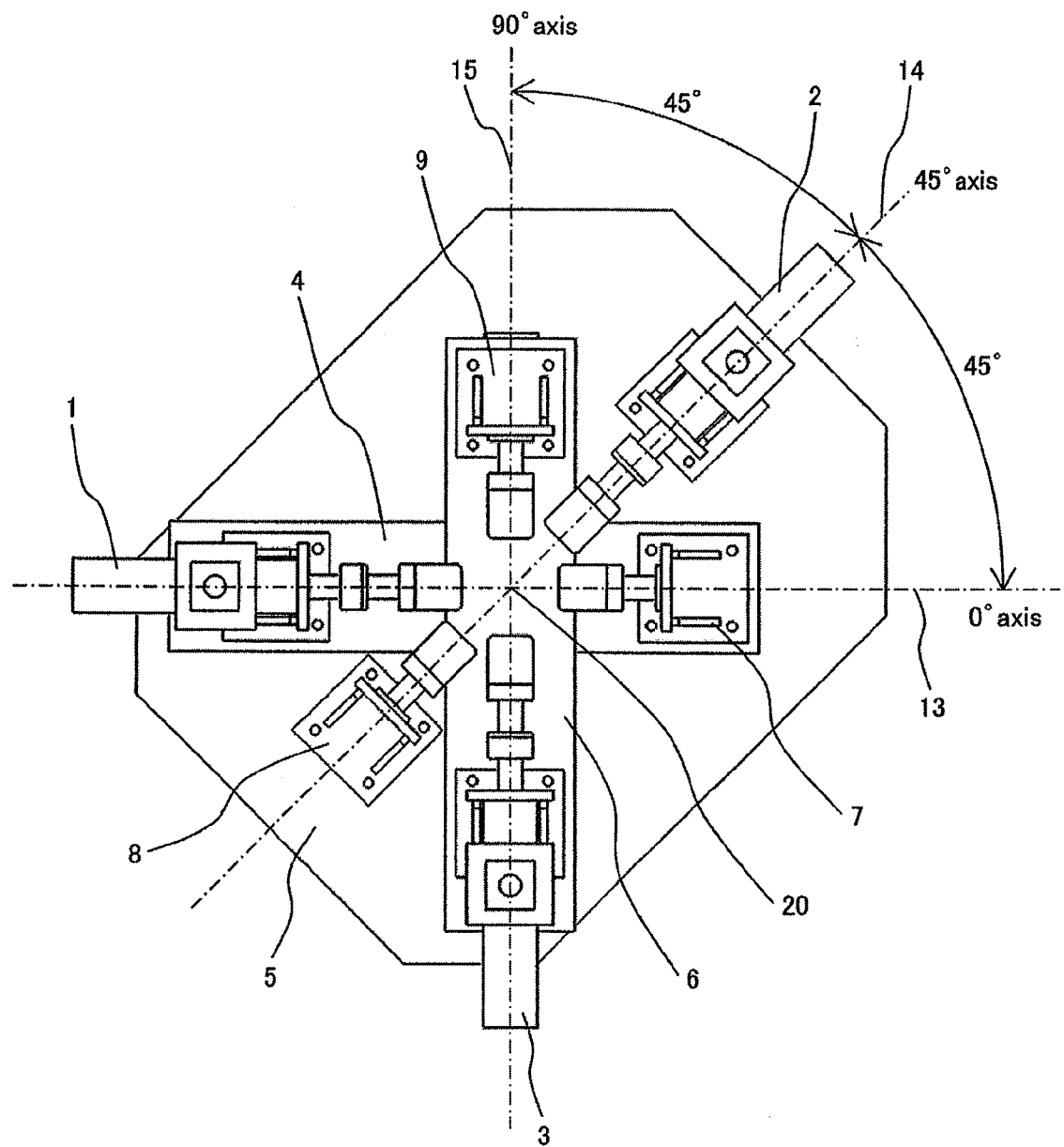
FIG. 3 is a plane view for showing the first example of the structure of the strength testing apparatus according to the first embodiment.
Figure 4:
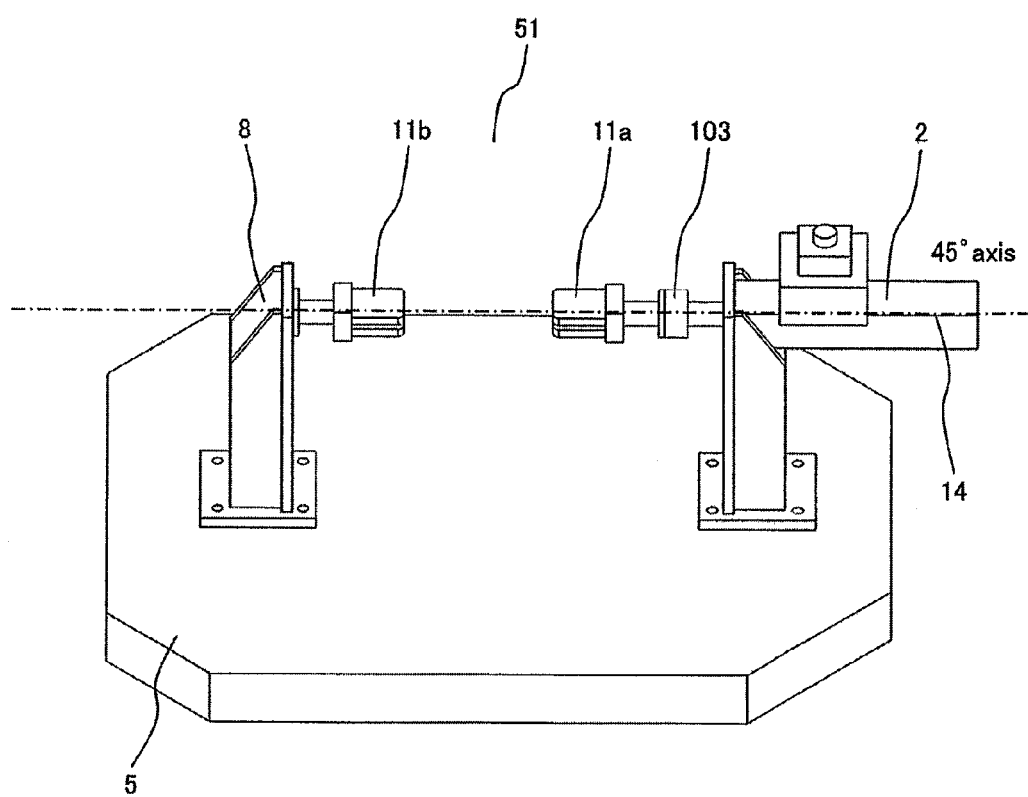
FIG. 4 is a perspective view for showing only a testing structure of 45°-axis, while extracting it from the first example of the structure of the strength testing apparatus according to the first embodiment.
Figure 5:
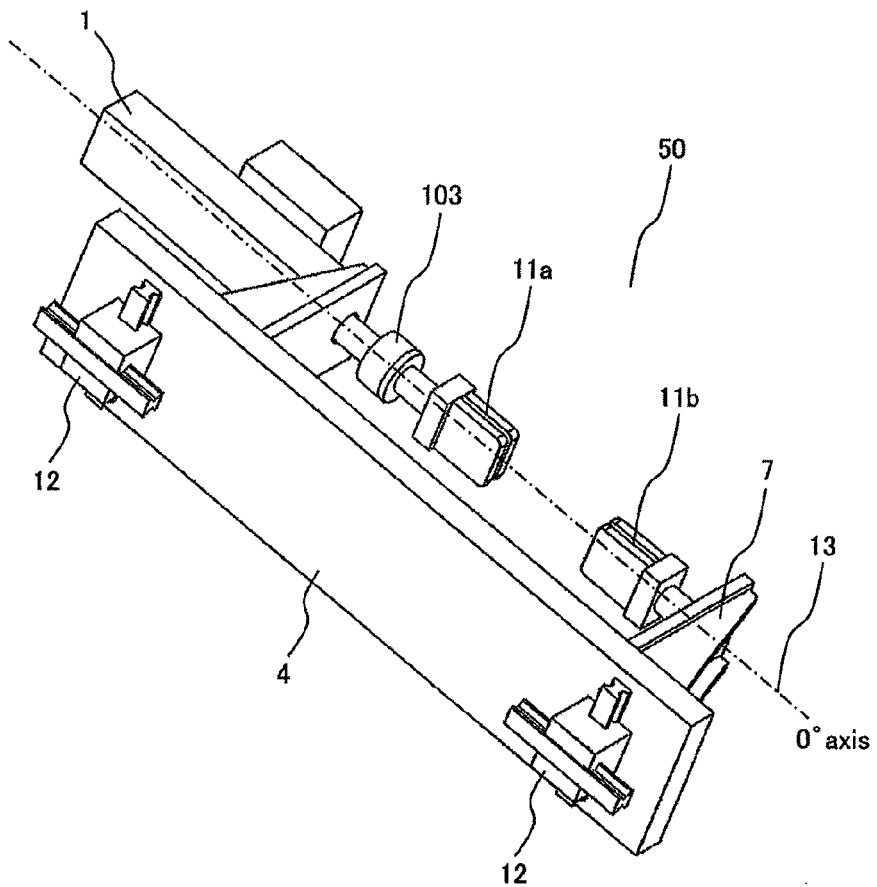
FIG. 5 is a perspective view for showing a testing structure of 0°-axis, while only extracting it from the first example of the structure of the strength testing apparatus according to the first embodiment.
Figure 6:
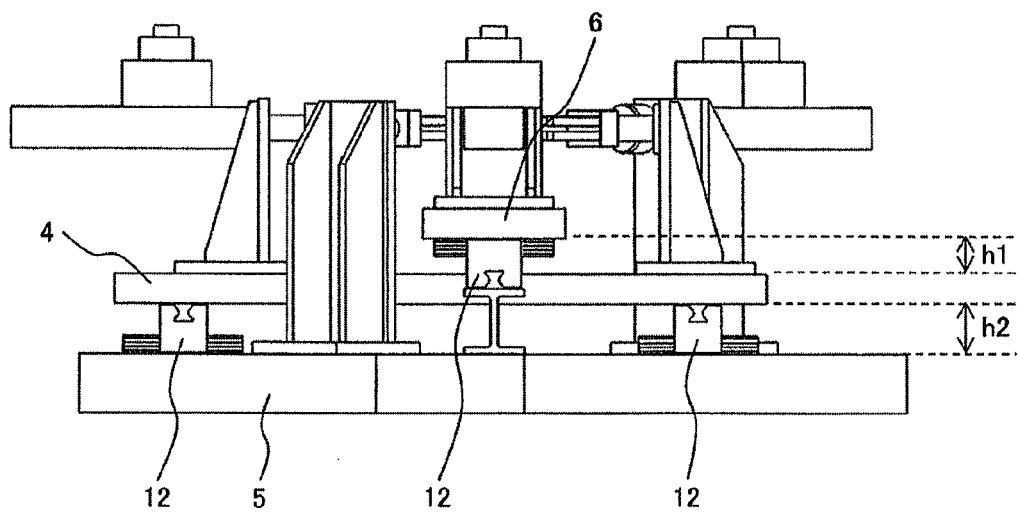
FIG. 6 is a front view for showing the first example of the structure of the strength testing apparatus according to the first embodiment.
Figure 7:
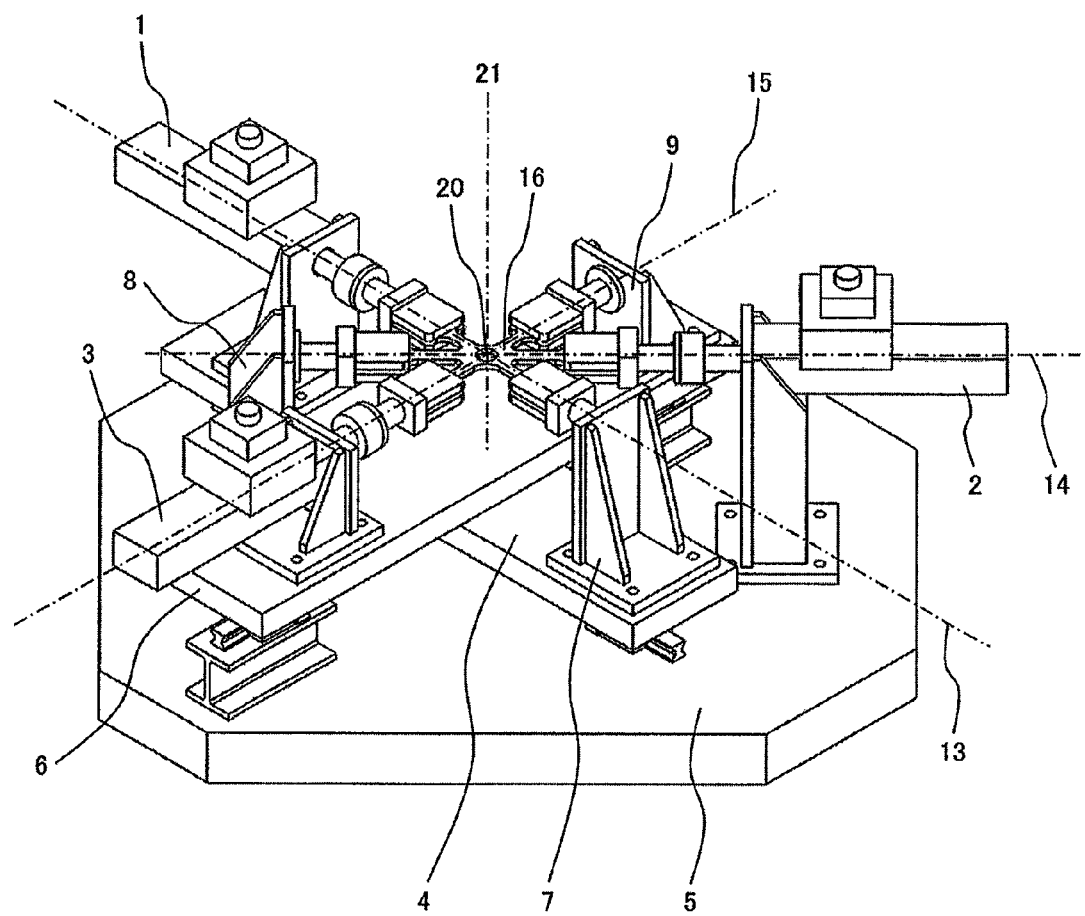
FIG. 7 is a perspective view for showing the case where a test piece is attached on the first example of the structure of the strength testing apparatus according to the first embodiment.
Figure 8:
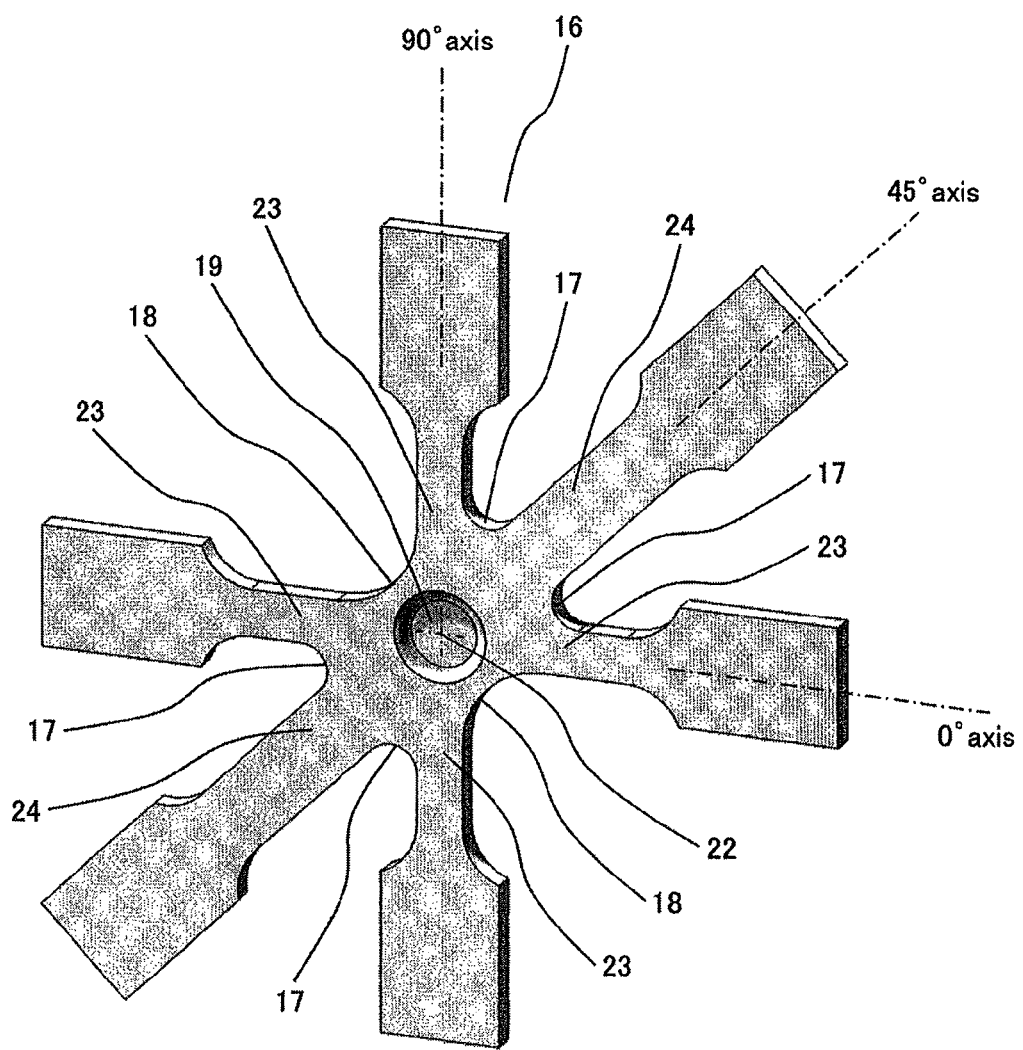
FIG. 8 is a perspective view for showing the test piece to be tested by means of the first example of the structure of the strength testing apparatus according to the first embodiment.
Figure 9:
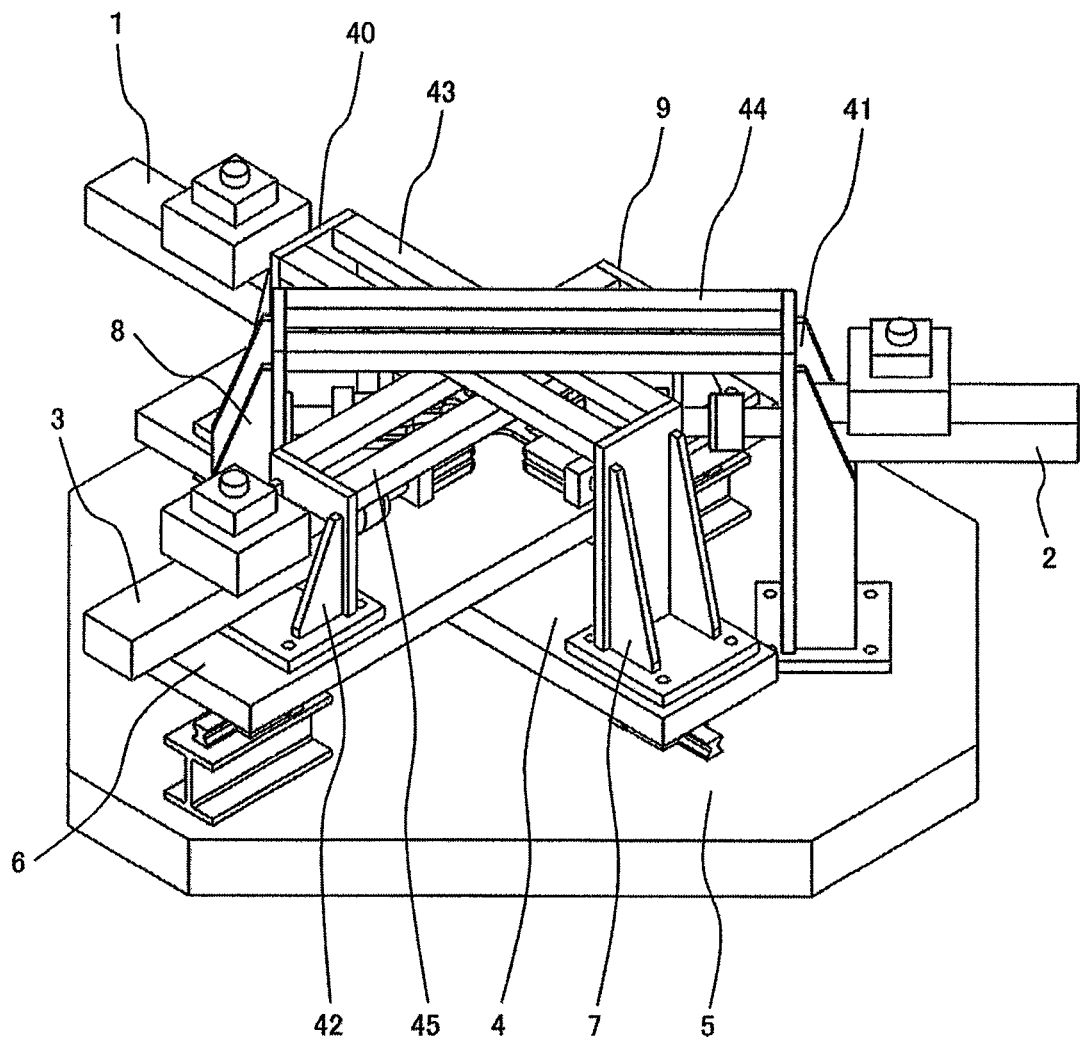
FIG. 9 is a perspective view for showing an example of the structure, deriving from the first example of the structure of the strength testing apparatus according to the first embodiment.
Figure 10:
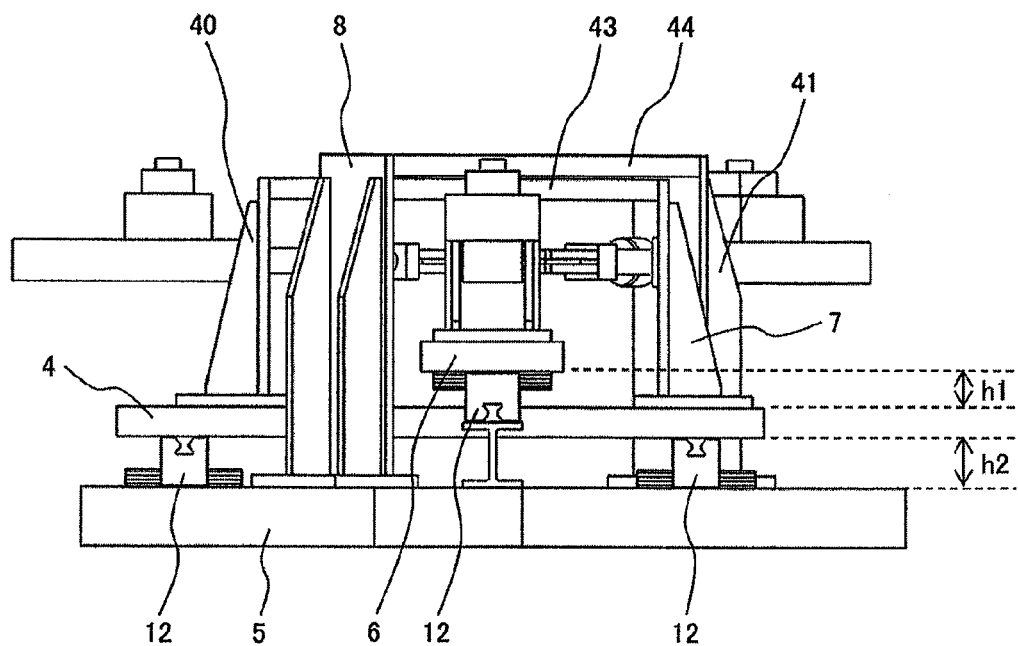
FIG. 10 is a front view for showing the example of the structure deriving from the first example of the structure of the strength testing apparatus according to the first embodiment.
Figure 11:
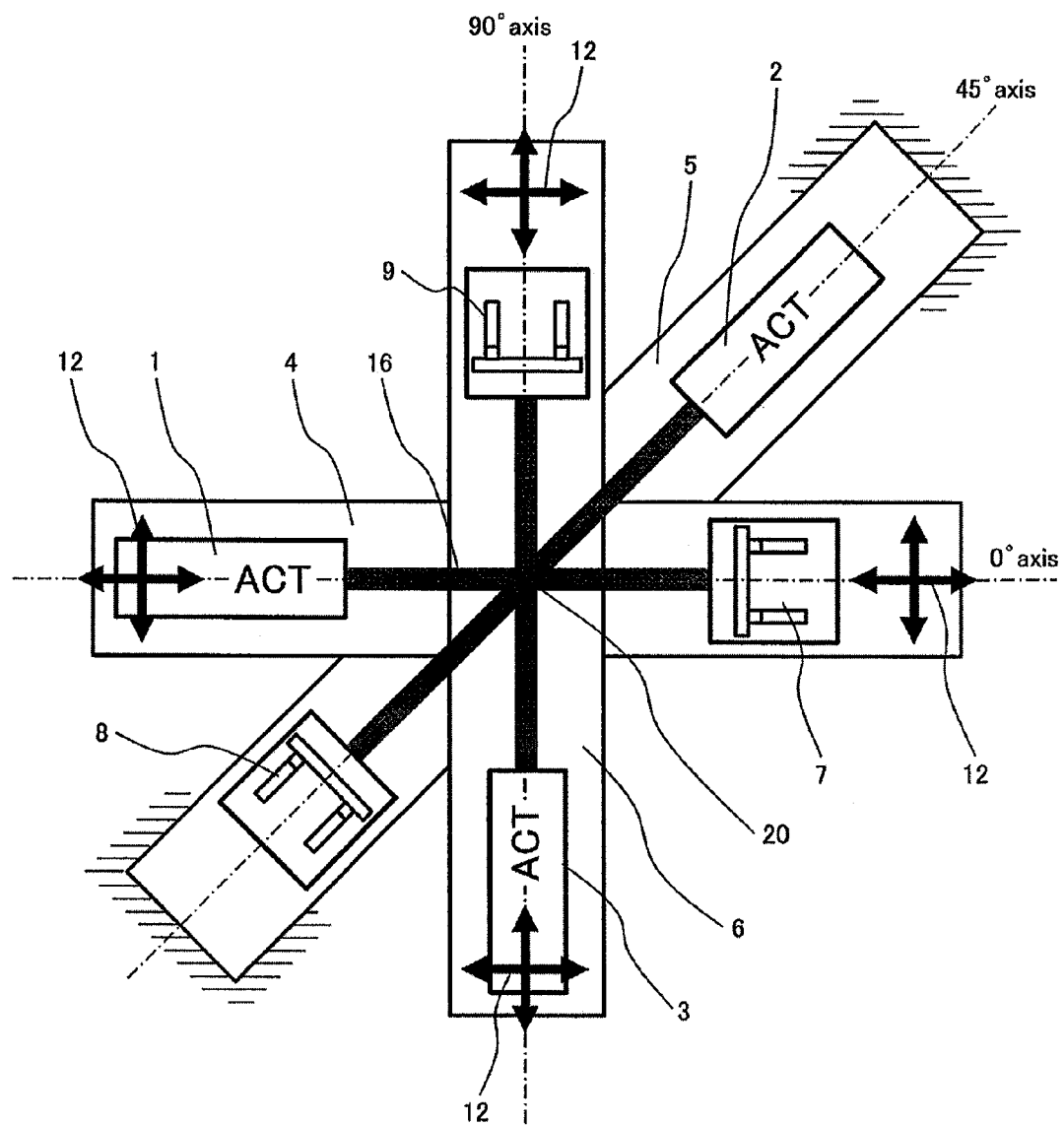
FIG. 11 is a block diagram for showing the first example of the structure of the strength testing apparatus according to the first embodiment.

Hereinafter, explanation will be given on a first example of the structure of the strength testing apparatus according to a first embodiment of the present invention, by referring to FIGS. 2 to 11. Herein, FIG. 2 is a perspective view of the main body frame of the strength testing apparatus; FIG. 3 is a plane view of the main body frame shown in FIG. 2, when viewing it in the direction orthogonal to a plane, on which the main body frame is installed (e.g., a plane in parallel with a plane including all the testing axes therein); FIGS. 4 and 5 are views for showing different 1-axis testing structures, which are extracted from the main body frame shown in FIG. 2; FIG. 6 is a front view of the main body frame shown in FIG. 2, when viewing it into the direction in parallel with the installation plane thereof; FIG. 7 is a perspective view, in case of attaching a test piece on the main body frame shown in FIG. 2; FIG. 8 is a perspective view of the test piece; FIG. 9 is a perspective view when a rigidity assistant member onto the main body frame shown in FIG. 2; FIG. 10 is a front view of FIG. 9 viewing the main body frame in the same direction to FIG. 2; and FIG. 11 is a view for showing the main constituent elements of the main body frame shown in FIG. 2, diagrammatically.

The main body frame 101, as is shown in FIGS. 2 and 3, includes three (3) sets of actuators 1, 2 and 3, three (3) sets of actuator fixing bases 40, 41 and 42, three (3) sets of reaction bases 7, 8 and 9, and three (3) sets of bases 4, 5 and 6; i.e., building up three (3) sets of 1-axis testing structures. Namely, the actuator 1, the actuator fixing base 40 and the reaction base 7 are connected with the base 4, thereby achieving the testing structure of 0°-axis 13; the actuator 2, the actuator fixing base 41 and the reaction base 8 are connected with the base 5, thereby achieving the testing structure of 45°-axis 14; the actuator 3, the actuator fixing base 42 and the reaction base 9 are connected with the base 6, thereby achieving the testing structure of 90°-axis 15, respectively. Those three (3) sets of the 1-axis testing structures are so arranged, that the 0°-axis 13 and the 45°-axis 14 define an angel 45° therebetween, and the 45°-axis 14 and the 90°-axis 15 also define the angel 45° therebetween, respectively. Testing axes, each passing through almost an axial center of the actuators 1, 2 and 3, correspond to the 0°-axis 13, the 45°-axis 14 and the 90°-axis 15, respectively, and those intersect with one another at an axial intersection point 20 and are included on the same plane.

FIGS. 4 and 5 are views of a testing structure of the 45°-axis 14 and a testing structure of 0°-axis 13, which are extracted from the main body frame shown in FIG. 2. The actuators 1, 2 and 3 make translatory movement, so as to generate a load to be applied onto the test piece, and at each end thereof is equipped a chucking tool 11*a*. Other chucking tool 11*b*, coupling with this chucking tool 11*a*, is installed on the reaction base 7, 8 or 9, and the test piece is chucked by the chucking tools 11*a* and 11*b*. Also, in order to detect a magnitude of the load that the actuator generates, the load cell 103 is disposed between the actuator and the chucking tool 11*a*. In this example of the structure, the load cell 103 is disposed between the actuator and the chucking tool 11*a*; however it may be disposed between the reaction base 7, 8 or 9 and the chucking tool 11*b*.

The base 5 included in the testing structure of 45°-axis 14 is fixed in the position thereof. On the other hand, on the base 4, which is included in the testing structure of 0°-axis 13, and the base 6, which is included in the testing structure of 90°-axis 15, are equipped with 2-axes linear guides 12, as is shown in FIG. 5. Also, the bases 4, 5 and 6 are disposed in parallel with a plane, including the testing axes 13, 14 and 15 therein, and as is shown in FIG. 6, a gap of distance "h2" is provided between the bases 4 and 5, while a gap of distance "h1" is provided between the bases 4 and 6, respectively. In this manner, each base is arranged so that no interference occurs therebetween, and further by means of those 2-axes linear guides 12, the testing structure of 0°-axis 13 including the base 4 therein, and the testing structure of 90°-axis 15 including the base 6 therein are able to move in parallel with the plane including the testing axes 13, 14 and 15, under the condition that no test piece is attached thereon.

As is shown in FIG. 7, the test piece 16 shown in FIG. 8 is chucked by the chucking tools, in such a manner that an axis, being perpendicular to the plane including the testing axes 13, 14 and 15, can pass through a center 22 of the test piece, and thereby to be tested. The test piece 16 has the configuration of extending the end portions thereof, from the center of the test piece, into the directions of the testing axes; e.g., 0°, 45° and 90°, respectively. In a central area 19 of the test piece 16 can be reproduced an arbitrary multi-axes stress condition, which will appear on the surface of a plate building up the structure, by means of those actuators 1, 2 and 3.

Herein, explanation will be made on a principle or theory of generating the multi-axes stresses, by the three (3) sets of the 1-axis testing structures, briefly. It is defined that the vertical stresses in the directions 0°, 45° and 90°, being generated in the central area 19 of the test piece 16 by means of a load of 1 kN of the actuator 1, which is included in the testing structure of 0°-axis 13, are "σ0-0ACT", "σ45-0ACT" and "σ90-0ACT", respectively. In similar manner, it is also defined that the vertical stresses in the directions 0°, 45° and 90°, by the load of 1 kN of the actuator 2, which is included in the testing structure of 45°-axis 14, are "σ0-45ACT", "σ45-45ACT" and "σ90-45ACT", and further that the vertical stresses in the directions 0°, 45° and 90°, by the load of 1 kN of the actuator 3, which is included in the testing structure of 90°-axis 15, are "σ0-90ACT", "σ45-90ACT" and "σ90-90ACT", respectively. In case where the loads generated by the actuators 1, 2 and 3 are "αkN", "βkN" and "γkN", respectively, then the multi-axes stresses, which will occur in the central area of the test piece can be written by the following equations.

$$\sigma 0 = \alpha \cdot \sigma 0\text{-}0ACT + \beta \cdot \sigma 0\text{-}45ACT + \gamma \cdot \sigma 0\text{-}90ACT \qquad \text{(Eq. 1)}$$

$$\sigma 45 = \alpha \cdot \sigma 45\text{-}0ACT + \beta \cdot \sigma 45\text{-}45ACT + \gamma \cdot \sigma 45\text{-}90ACT \qquad \text{(Eq. 2)}$$

$$\sigma 90 = \alpha \cdot \sigma 90\text{-}0ACT + \beta \cdot \sigma 90\text{-}45ACT + \gamma \cdot \sigma 90\text{-}90ACT \qquad \text{(Eq. 3)}$$

Where, "σ0", "σ45" and "σ90" in those equations (1) to (3) are the vertical stresses, which will generate in the central area 19 of the test piece in the directions 0°, 45° and 90°, respectively. If grasping those "σ0-0ACT", "σ0-45ACT", "σ0-90ACT", "σ45-0ACT", "σ45-45ACT", "σ45-90ACT", "σ90-0ACT", "σ90-45ACT" and "σ90-90ACT", in advance, through an experimentation or numerical analysis, for example, as is apparent from those equations (1) to (3) mentioned above, it is possible to generate arbitrary multi-axes stresses, "σ0", "σ45" and "σ90", in the central area 19, by changing the loads of the actuators 1, 2 and 3 (e.g., changing α, β, γ).

For the purpose of conducting the fatigue test under such multi-axes stress conditions, the plate thickness of the test piece 16 is determined to be thin, in the central area 19 thereof, comparing to that of the chucking portions and the arm portions 23 and 24, i.e., the fatigue failure can be generated, easily, from that central area 19. In case where no movable mechanism is equipped on the bases 4 and 6, bending stresses act upon the arm portions 23 and 24, and then high stresses are generated at joints 17 an 18 of the arm portions 23 and 24. Such bending deformations of the arm portions 23 and 24 are the deformations generating within the surface of the test piece 16. As a result of such bending deformation generating within the surface, the fatigue failures occur at the joints 17 and 18, but not under the multi-axes stress condition, on the contrary to an original purpose, i.e., conducting the fatigue test under the multi-axes stress condition. In the example of the present structure, because the intersection point 20 of the testing axes is automatically adjusted to the central area of the test piece during the time of testing, it is possible to generate the fatigue failure from the central area 19.

Also, if not increasing the rigidity of the base to be high, the base is deformed largely, due to the load that the actuator generates, and depending on the situation, this deforms the test piece 16 into the direction of the plate thickness thereof, and thereby generates unexpected stresses in the central area 19. For avoiding such deformation in an outside of the surface of the test piece 16, it is enough to adopt the structure, for the bases 4, 5 and 6 to be high in the rigidity thereof. However, as the result of increasing the rigidity of those bases 4, 5 and 6, which are included in the movable testing structure, if the mass of those comes to be large, then movability of the testing structures of the 0°-axis and the 90°-axis, which are movable, comes to be bad, and it is difficult to conduct the fatigue test at high repetitive frequency. In such case, as is shown in FIGS. 9 and 10, it is possible to prevent the test piece 16 from being deformed in the outside of the surface thereof, if connecting the fixing bases 40, 41 and 42 and the reaction bases 7, 8 and 9, on the side of the actuator, by rigidity assistant members 43, 44 and 45, in a manner of light-weight, comparing to the case of only increasing the rigidity of the bases to be high. Adoption of a bold connection or the like, being detachable, as the connecting structure for those rigidity assistant members 43, 44 and 45, enables an operation under the condition of removing those rigidity assistant members, when chucking or detaching the test piece 16. In FIG. 10, since those rigidity assistant members 43, 44 and 45 (not shown in the figure) are arranged to keep a gap, respectively, among of those, so that no interference occurs therebetween, therefore those rigidity assistant members never block the movements of the bases 4 and 6. In FIGS. 9 and 10, for the 1-axis testing structure, the fixing base and the reacting base on the side of the actuator are connected by two (2) pieces of the rigidity assistant members, and all of those rigidity assistant members are rectangle, in the cross-section shapes thereof. The number of those rigidity assistant members and the shape of the cross-section thereof should not be restricted to this example of the structure thereof, may be determined to the number and/or the shape, corresponding to the load that actuators generate, the rigidity of the bases, and the rigidity of the test piece.

Figure 12:
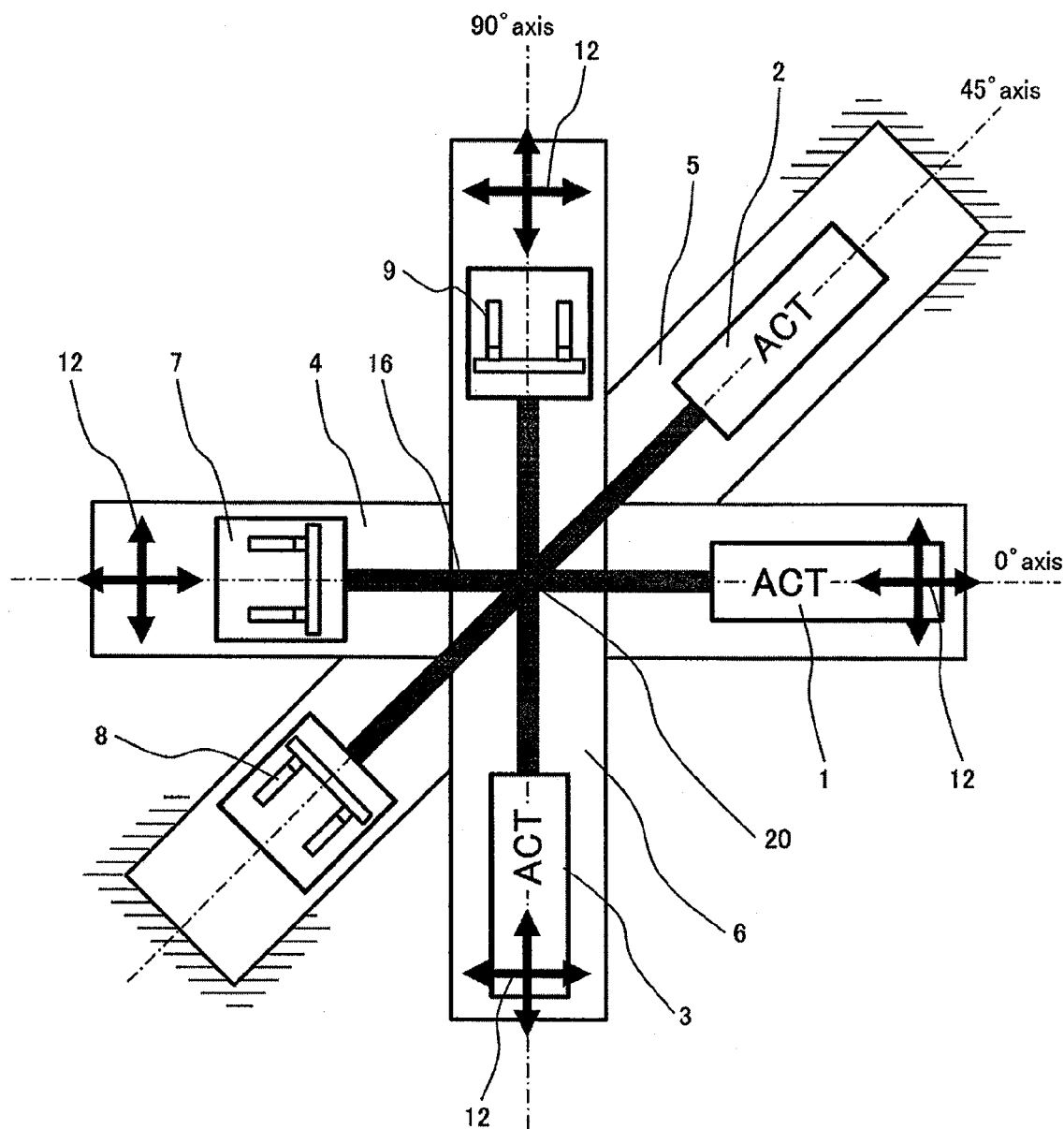
FIG. 12 is a block diagram for showing the first example of the structure, deriving from the first example of the structure of the strength testing apparatus according to the first embodiment.

FIG. 11 is a block diagram for showing the arrangement of the actuators 1, 2 and 3, which are main constituent elements of the main body frame 101, the reacting bases 7, 8 and 9, the bases 4, 5 and 6, and a 2-axes linear guide 12, on a plane, wherein angular positions of the testing axes are depicted, correctly, similar to those on the plane view of FIG. 3. An actuator 1 and an actuator 2 are arranged in such a manner that an angular gap between them is 135°, and actuators 1 and 3 are arranged at an angular gap 90°, however, as is shown in FIG. 12, they may be so arranged that the angular gap comes to 45° between the actuators 1 and 2 while the angular gap 90° between the actuators 1 and 3. Namely, the actuator and the reacting base, which are connected onto the same base, are able to generate the multi-axes stress condition in the central area 19, in the similar manner to the present example of structure, without generating the high stresses due to the bending loads at the joints 17 and 18 of the test piece 16, even if being positioned on any side, on a boundary of the axial intersection point 20. Also, in the present example of structure, the base 6, which is included in the 90°-axis testing structure, is disposed at the most front side from a paper surface, on the plane views shown in FIGS. 3, 11 and 12, and at the uppermost portion of the paper surface of the front view shown in FIG. 6. On the contrary, if the base 4, which is included in the 0°-axis testing structure, is disposed on the most front side on the plane views, and is disposed at the uppermost portion on the front view, it is also possible to achieve the similar function to that of the apparatus of the present example of structure. In this manner, the positional relationship, defined between the plane, including the testing axes of the bases 4, 5 and 6, and the vertical direction, should not limited, in particular, to that of the present example of structure; but, as far as those bases are so arranged that no interference occurs with each other, there can be obtained the effect of the present invention. Further, in the present example of structure, the 45°-axis testing structure is fixed in the position thereof, while the 0°-axis and the 90°-axis testing structures are movable with attaching the 2-axes linear guide 12 onto the bases 4 and 6; however, if rendering the testing structures of other two (2) axes movable, there can be also obtained the effect of the present invention, even if selecting any of those axes to be fixed in the position thereof.

In the manner of the present example of structure, if applying only the 0°-axis testing structure 13 and the 90°-axis testing structure 15, as merit or advantage of arranging the three (3) sets of the 1-axis testing structures at the angular positions 0°, 45° and 90°, respectively, on the plane shown in FIGS. 3 and 11, there can be listed up an aspect that the strength test can be implemented for the two (2) axes loads described in the Non-Patent Document 1, too.

Figure 13:
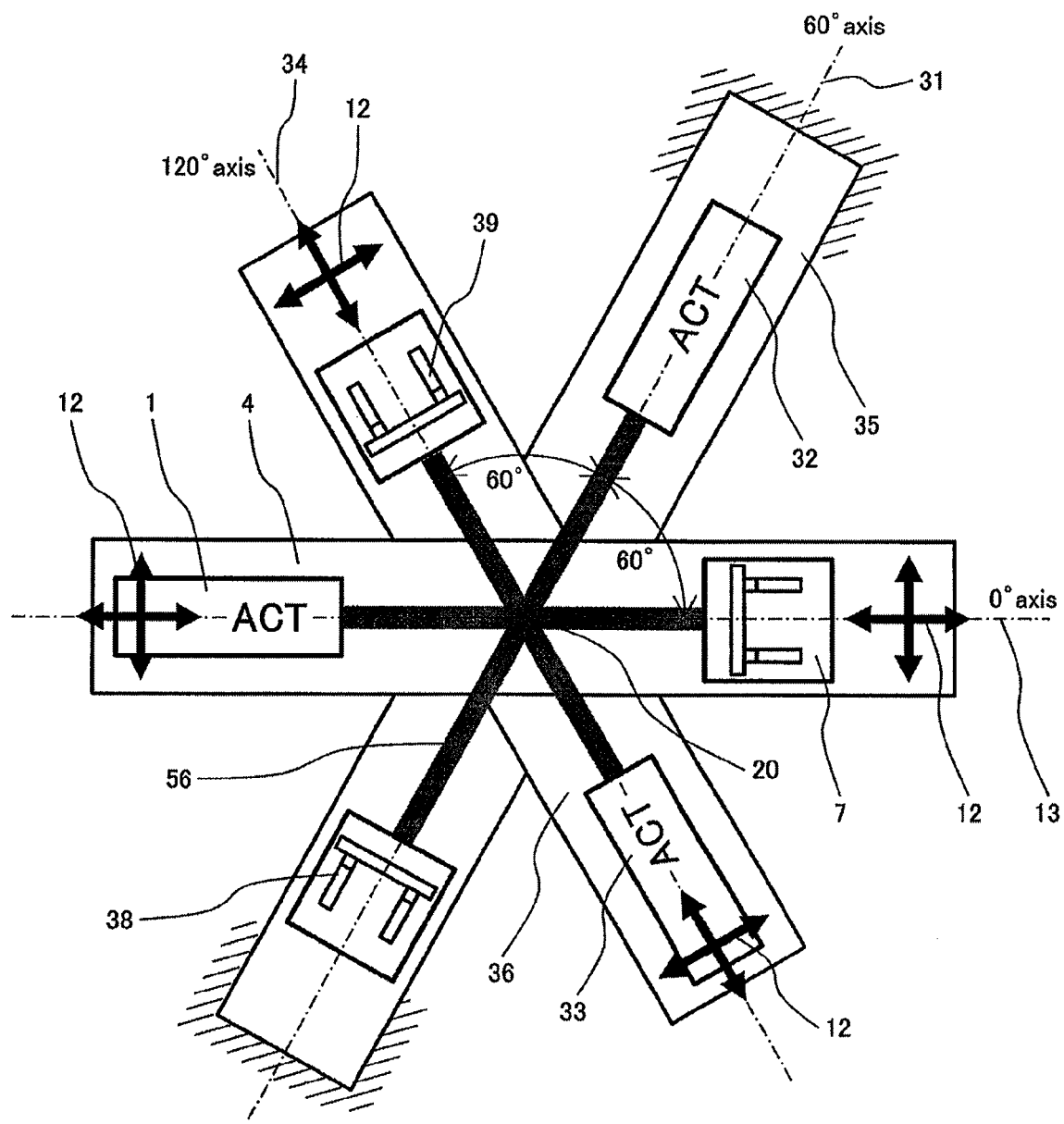
FIG. 13 is a block diagram for showing a second example of the structure of the strength testing apparatus according to the first embodiment.

Next, explanation will be given about a second example of structure of the strength testing apparatus, according to the first embodiment of the present invention, by referring to FIG. 13. This FIG. 13 is a view, in the similar manner of showing the first example of structure, diagrammatically, in FIG. 11, for showing the main constituent element of the main body frame, diagrammatically, relating to the second example of structure.

Similar to the first example of structure of the first embodiment, there are included actuators 1, 32, 33, reaction bases 7, 38 and 39, and bases 4, 35 and 36, and they achieve the testing structure having three (3) axes. Testing axes 13, 31 and 34, each passing through almost of the axial center of the actuator, come across at the axial point 20, and they are included on the same plane. However, in the first example of structure, although the testing axes are arranged at the angular positions of 0°, 45° and 90°, on the plane including the testing axes, as is shown in FIGS. 3 and 11; however, in the second example of structure, the testing axes are arranged at 0°, 60° and 120°, on the same plane. Even with such arrangement of the 1-axis testing structures, it is possible to achieve the effect of the invention, which is similar to that of the first example of structure. As a merit or advantage of this second example of structure, since an angle between the testing axes can be widen from 45° to 60°, it is possible to arrange the constituent elements of the main body frame 101, with keeping sufficient margin among them, comparting to the first example of structure of the first embodiment. Also, a test piece 56 adopts the configuration, extending the end portions thereof, from the center of the test piece to the directions of the testing axes; i.e., 0°, 60° and 120°, and with such configuration, comparting to that shown in FIG. 8, since all of angles defined between the arm portions of the test piece come to 60°, then the joint 17 of the arm portion can be easily prevented from the fatigue failure thereof, by the high stress caused due to the bending load.

<Embodiment 2>

Figure 14:
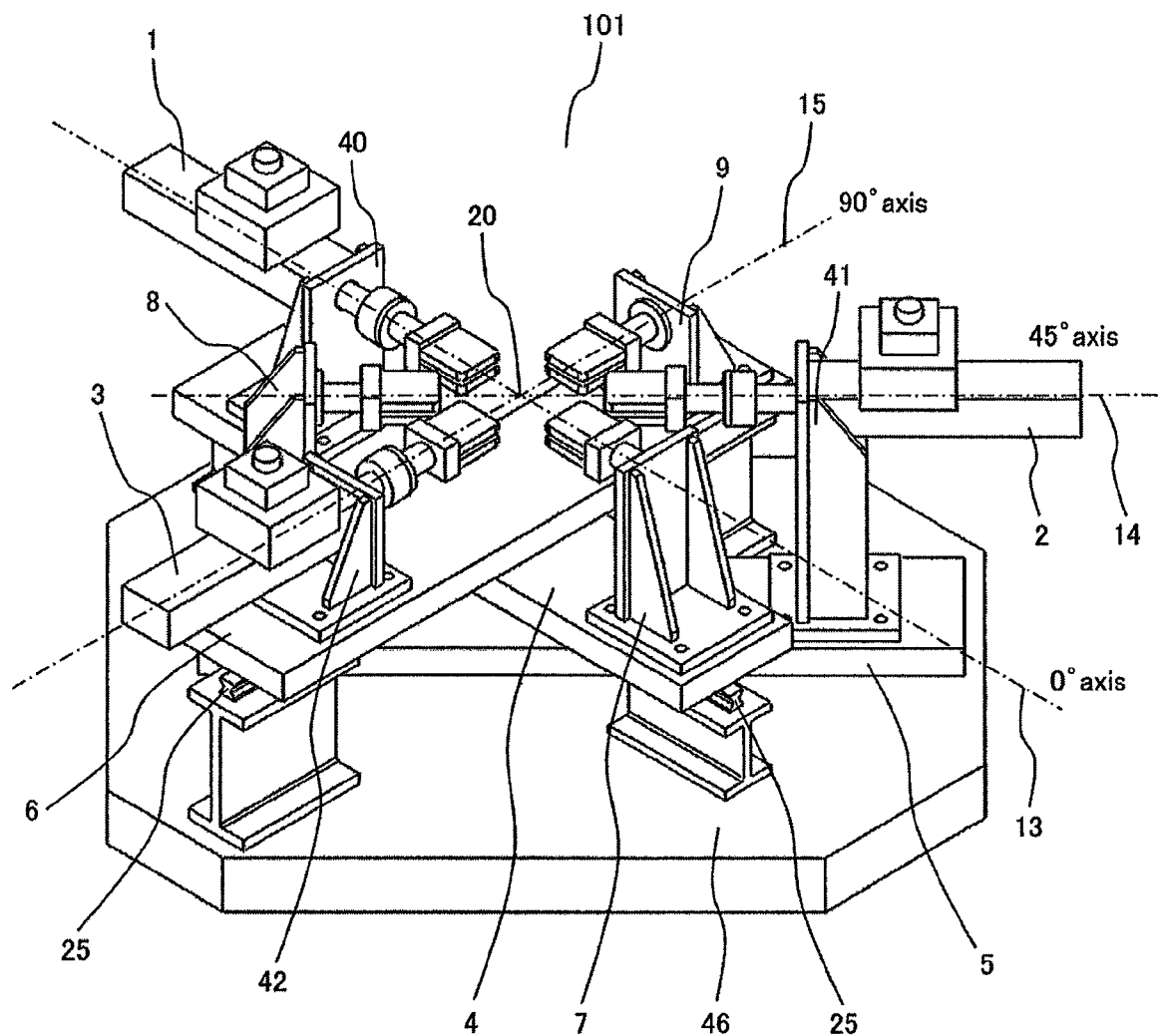
FIG. 14 is a perspective view for showing a first example of the structure of the strength testing apparatus according to a second embodiment.
Figure 15:
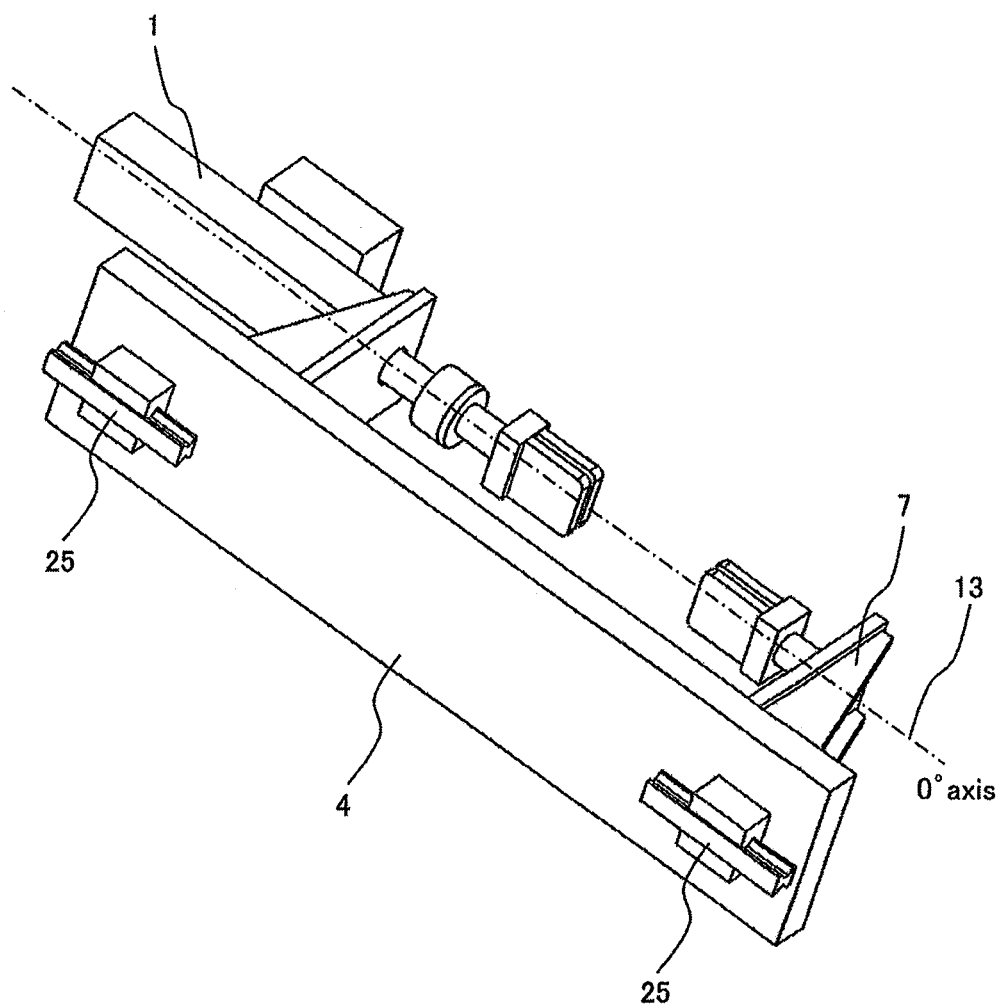
FIG. 15 is a perspective view for showing a testing structure of 0°-axis, while only extracting it from the first example of the structure of the strength testing apparatus according to the second embodiment.
Figure 16:
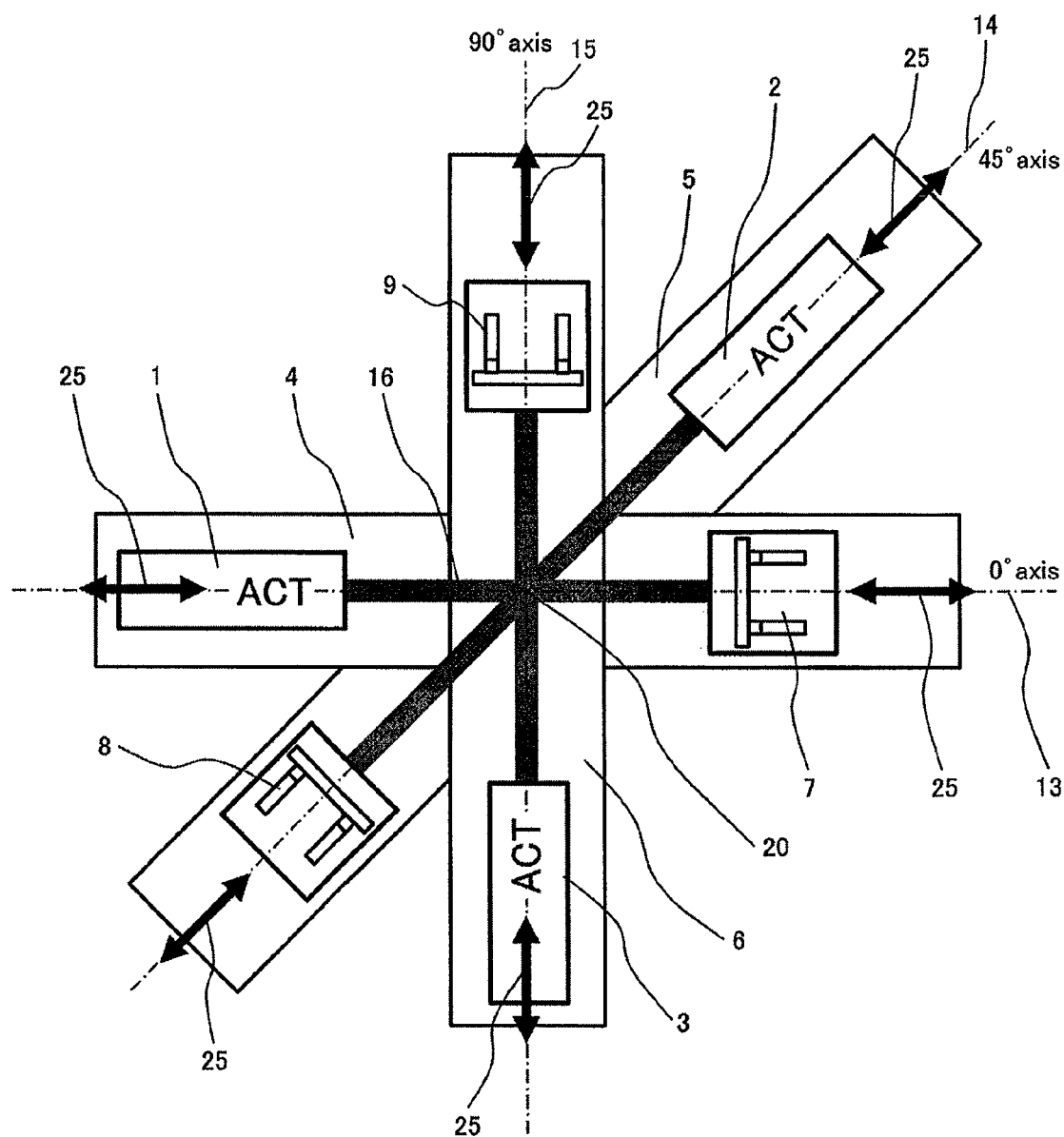
FIG. 16 is a block diagram for showing a first example of the structure of the strength testing apparatus according to the second embodiment.

Next, explanation will be given on a first example of structure of the strength testing apparatus, according to a second embodiment of the present invention, by referring to FIGS. 14 to 16. FIG. 14 is a perspective view of the main body frame 101, according to the present example of structure; FIG. 15 is a view for showing the 1-axis testing structure, which is extracted from the main body frame; and FIG. 16 is a block diagram for showing only the main constituent elements among those in the main body frame of the present example of structure. In FIG. 16, the angular positions of the constituent elements are correctly depicted on the plane including the testing axes, in the similar manner to that shown in FIGS. 11 to 13. This is also same to the first example of structure, in the characteristics thereof, for example, that all of the testing axes are included on the same plane, and they also come across at one (1) point, e.g., the axial intersection point 20, and that the 1-axis testing structure, which is movable in parallel with the plane including the testing axes, can move, etc.

For the purpose of preparing the 1-axis testing structure by three (3) sets thereof, similar to that in the first embodiment, the main body frame 101 includes therein, the actuators 1, 2 and 3, the actuator fixing bases 40, 41 and 42, and the reaction bases 4, 5 and 6. Also, as is shown in FIG. 6 relating to the first example of the first embodiment, the bases 4, 5 and 6 are disposed at positions, differing from one another, in the direction perpendicular to the plane including the testing axes; i.e., it is also similar to the example of structure of the first embodiment, in particular, in an aspect that those bases do not interfere with one another even if the testing structures are movable. However, differing from the first embodiment, all of the 1-axis testing structures are set to be movable into the testing axes thereof. Namely, the testing structure of 0°-axis 13 is attached on a 1-axis linear guide 25, so that it can move linearly in the 0°-axis direction. Also, in the similar manner, for the testing structures of 45°-axis 14 and 90°-axis 15, the 1-axis linear guides 25 are attached on the bases thereof, so that they can move linearly in the 45°-axis and the 0°-axis directions, respectively. With such arrangement of the linear guides onto those bases 4, 5 and 6, a load is acted on the test piece 16 by the actuators 1, 2 and 3, and even if the test piece 16 is deformed, the axial intersection point 20 can be kept at the same position, always, by the function of the 1-axis linear guides 25. As a result thereof, no bending load is applied on the arm portion of the test piece 16, and therefore, no fatigue failure is generated, unexpectedly, from the joints 17 and 18 of the arm portions of the test piece 16, during the testing.

In FIG. 16, although the base 6, which is included in the testing structure of 90°-axis 15, and the base 5, which is included in the testing structure of 45°-axis 14, are depicted, respectively, on the most front side from the paper surface of the figure and the deepest side therefrom; however, similar to the first embodiment, the positional relationship between the plane including the testing axes and the base in the vertical direction should not be limited to that shown in FIGS. 14 and 16. For example, when the base 4 or 5 is positioned at the most front side from the paper surface, there can be also obtained the effect according to the present invention without problems.

With this second embodiment, the main body frame 101 can be constructed with only a movable mechanism, which can move in a certain direction, such as, the 1-axis linear guide, etc. Because the 1-axis linear guide is small in the size thereof, comparing to that of the 2-axes linear guide 12, it is possible to make the distance "h1" or "h2" small, being defined between the bases shown in FIG. 6 of the first embodiment. If enabling to make the distance "h1" or "h2" between the bases small, since the bending load acting upon the reaction bases and/or the bases come to be small when testing, therefore it is possible to achieve the testing structure, being light-weight and high in the rigidity thereof, and thereby providing a strength testing apparatus for enabling the fatigue test at the high repetitive frequency. With the first embodiment, as is shown in FIG. 2, the movable testing structures of 0°-axis and 90°-axis can be installed on the base 5, the position of which is fixed, through the 2-axe linear guide 12. On the other hand, with the second embodiment, since all of the 1-xis testing structures are movable, there is a necessity of arranging the 1-xis testing structure, also for the base, which is included in the testing structure of 45°-axis.

Figure 17:
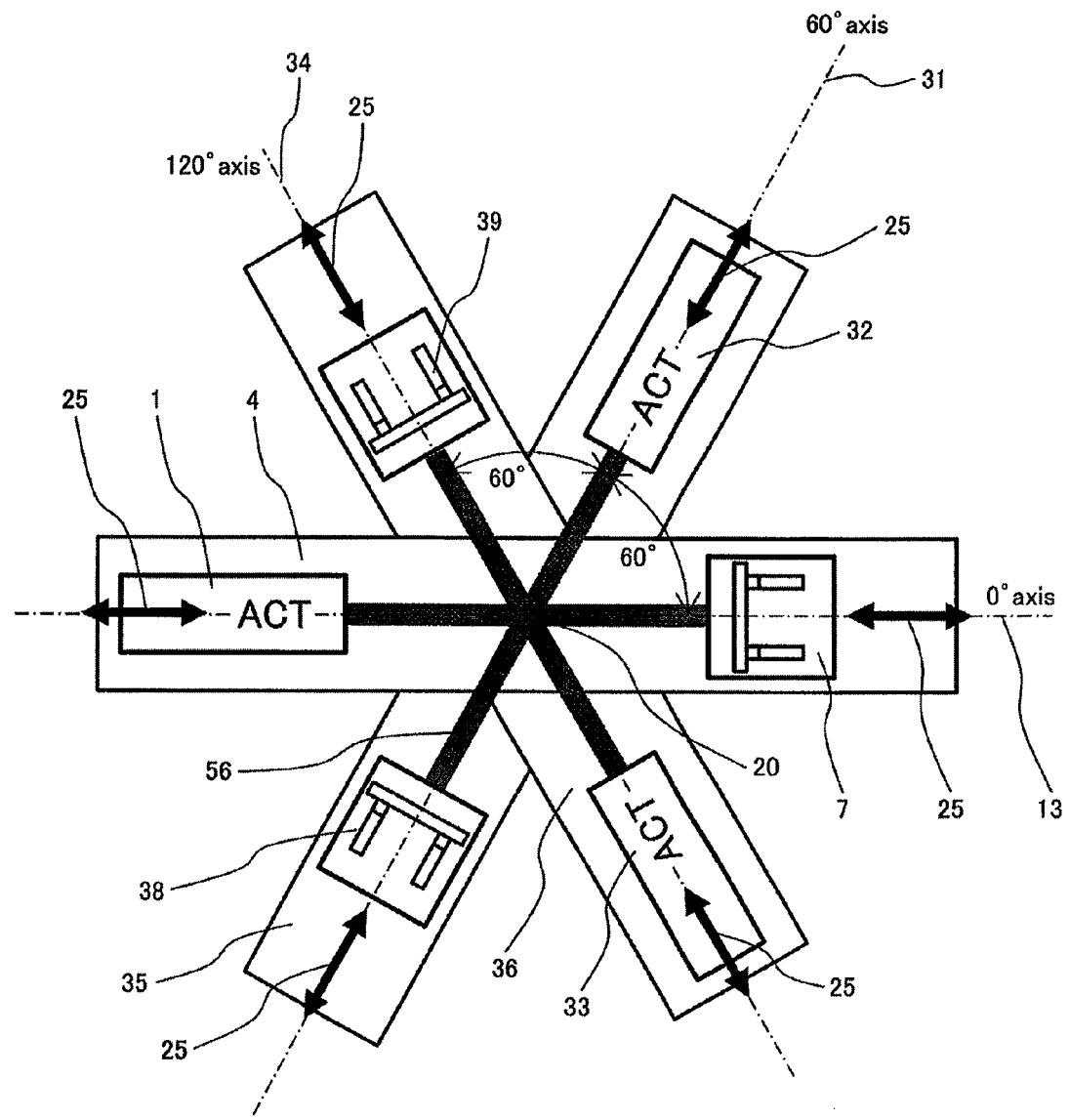
FIG. 17 is a block diagram for showing a second example of the structure of the strength testing apparatus according to the second embodiment.

FIG. 17 shows therein a second example of structure according to the second embodiment. In this example of structure, similar to the second example of structure according to the firs embodiment shown in FIG. 13, three (3) sets of the bases 4, 35 and 36 are arranged, so that three (3) pieces of the testing axes are separated from one another by an angle 60° on the plane including the testing axes. However, differing from the example of structure shown in FIG. 13, on each of the bases is attached the 1-axis linear guide 25, respectively, so that each the 1-axis linear guide 25 can move linearly into the direction of testing axis there. In the present example of structure, similar to the first example of structure according to the second embodiment, the axial intersection point 20 can be kept always at the same position, during the testing, by means of the 1-axis linear guide 25, and no bending load acts on the arm portion of the test piece 56. Also, since the angular distance between the testing axes is wide, comparing to the first example of structure, it is possible to arrange the constituent elements of the testing apparatus, with keeping a sufficient margin therebetween.

<Embodiment 3>

Figure 18:
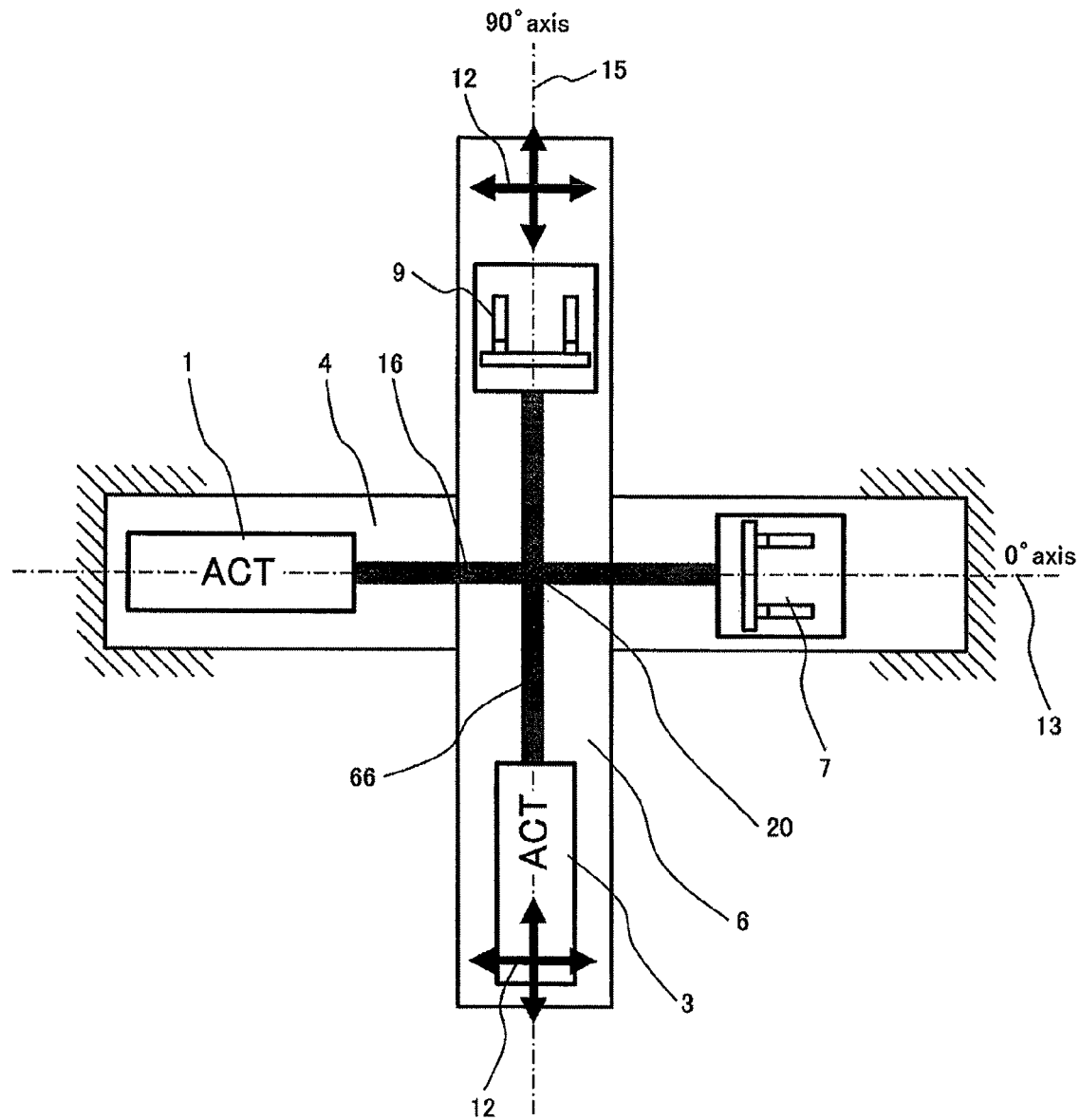
FIG. 18 is a block diagram for showing a first example of the structure of the strength testing apparatus according to a third embodiment.

Next, explanation will be given on a first example of structure of the strength testing apparatus, according to a third embodiment of the present invention, by referring to FIG. 18. This FIG. 18 is a block diagram for showing only the constituent elements, among the main body frame 101 of the present example of structure. In this FIG. 18, the angular positions of the constituent elements are depicted, correctly, on the plane including the testing axes, in the similar manner to that of the block diagrams shown in FIGS. 11 to 13. Thus, the following features are also same to those of the first and the second embodiments; i.e., that all of the testing axes are included on the same plane and they come across at one (1) point, e.g., the axial intersection point 20, and that the base can moves in parallel with the plane including the testing axes.

With the strength testing apparatus according to the third embodiment, the main body frame 101 has 2 (two) sets of the 1-xis testing structures. In the similar manner to those first and second embodiments, each testing structure includes actuators 1 and 3, actuator fixing bases (not shown in FIG. 18), reaction bases 7 and 9, bases 4 and 6, as the main constituent elements. The example of structure shown in FIG. 18 includes two (2) sets of the 1-xis testing structures, e.g., the testing structure of 0°-axis 13, and testing structure of 90°-axis 15. The testing structure of 0°-axis 13 is fixed in the position thereof; however, the testing structure of 90°-axis 15, on the base 6 of which is attached the 2-axes linear guides 12, can move in parallel with the plane including the testing axes. With such structure of the main body frame as mentioned above, it is possible to implement the test, being similar to the 2-axes test that is described in the Non-Patent Document 1, by two (2) pieces of actuators. Accordingly, the configuration of the test piece to be tested by the means of the strength testing apparatus, according to the third embodiment, is a cross-like shape expanding the arm portions from the central area thereof. In this example of structure, since the testing structure of 90°-axis 15, which is movable through the 2-axes linear guide 12, can be disposed on the base 4, the position of which is fixed, there is no need to prepare an installation surface, newly, for the purpose of providing the movable 1-axis testing structure thereon.

Figure 19:
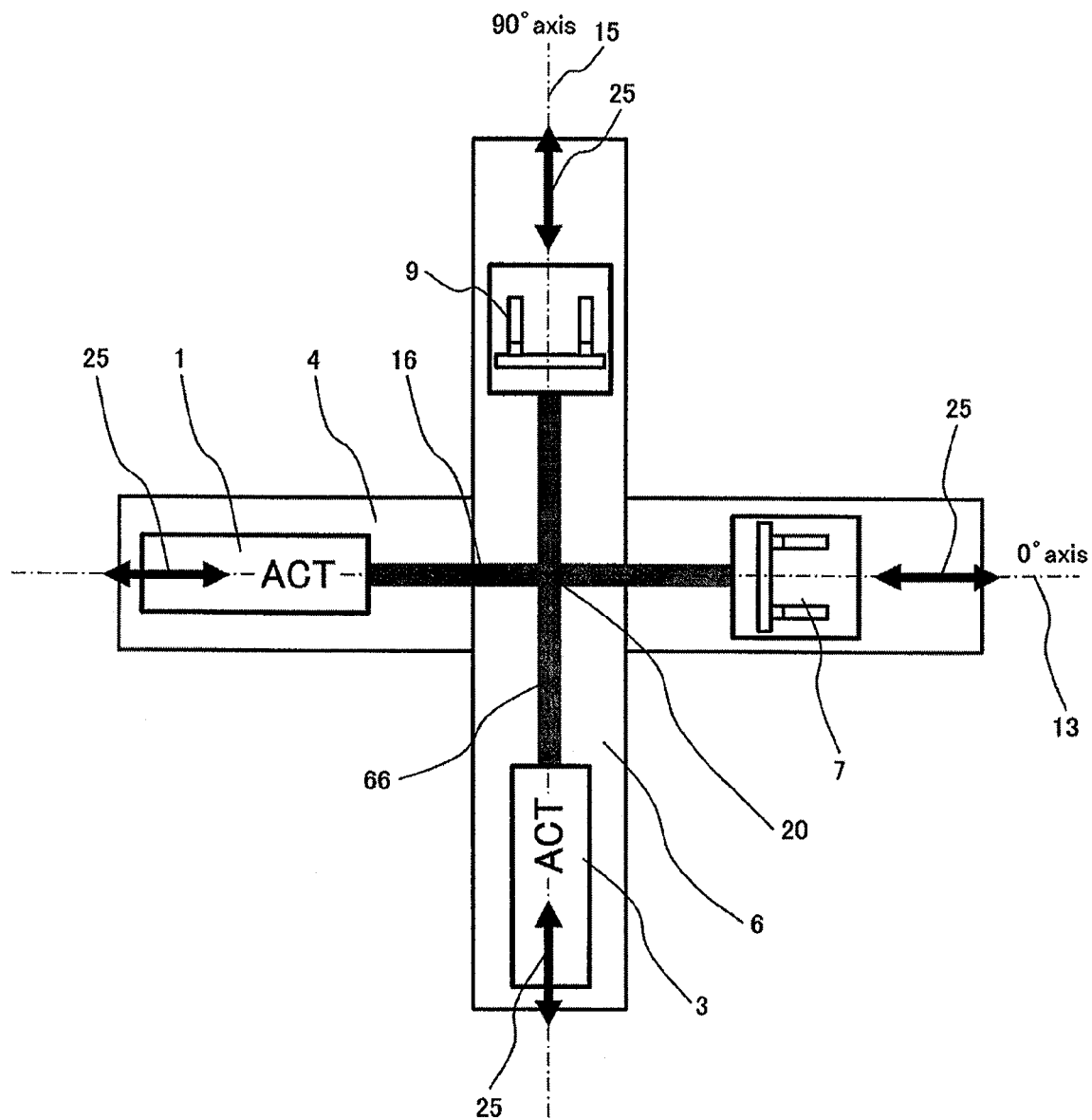
FIG. 19 is a block diagram for showing a second example of the structure of the strength testing apparatus according to the third embodiment.

FIG. 19 shows therein a second example of structure according to a third embodiment. This example of structure includes, similar to the example of structure shown in FIG. 18, wherein two (2) sets of the 1-axis testing structures, actuators 1 and 3, actuator fixing bases (not shown in FIG. 19), reaction bases 7 and 9 are the main constituent elements of each testing structure. Onto the base 4 included in the testing structure of 0°-axis 13, and the base 6 included in the testing structure of 90°-axis 15 are provided the 1-axis linear guides 25, and thereby achieving the respective linear movement into the testing axes, i.e., the 0°-axis 13 and the 90°-axis 15. With such arrangement of the linear guides as mentioned above, in the similar manner to that of the second embodiment, the load can be applied on the test piece by means of the actuator, but the axial intersection point 20 never moves, because of the movement of the 1-axis linear guides. As a result thereof, because of no bending load acting on the arm portion of the test piece 66, no high stress is generated at the junctions of the arm portions, and thereby generating the unexpected fatigue failure therefrom.

In the block diagrams of the examples 1 and 2 of structures shown in FIGS. 18 and 19, according to the third embodiment, the testing structure of the 90°-axis 15 is arranged at the most front side from the paper surface; however, the same effect of the invention can be obtained if the testing structure of the 0°-axis 13 is arranged at the most front side from the paper surface.

<Embodiment 4>

Further, explanation will be given on an example of structure of the strength testing apparatus according to a fourth embodiment of the present invention, by referring to FIG. 20. However, also in this FIG. 20, the same constituent elements, being same to those mentioned above, are shown with attaching the same reference numerals thereto. As is apparent from this figure, on ends of the actuators 1 and 3 and the reaction bases 7 and 9 are attached chucking tools 11a and 11b, respectively, and on the side of the actuator is provided a load cell 103. According to that fourth embodiment, differing from the embodiments mentioned above, in the movable 1-axis testing structure thereof, the actuator fixing bases 40 and 42 and the reaction bases 7 and 9 are connected with, through the plate-like base, but by means of rod-like bases 4 and 6, respectively. In addition thereto, in the other embodiment (s), although the 1-axis or the 2-axes linear guides are arranged, for the purpose of bringing the 1-axis testing structure to be movable, however, in the present embodiment, the linear guide 25 is arranged, not on the base(s), but on the actuator fixing bases 40 and 42 and the reaction bases 7 and 9.

Figure 20:
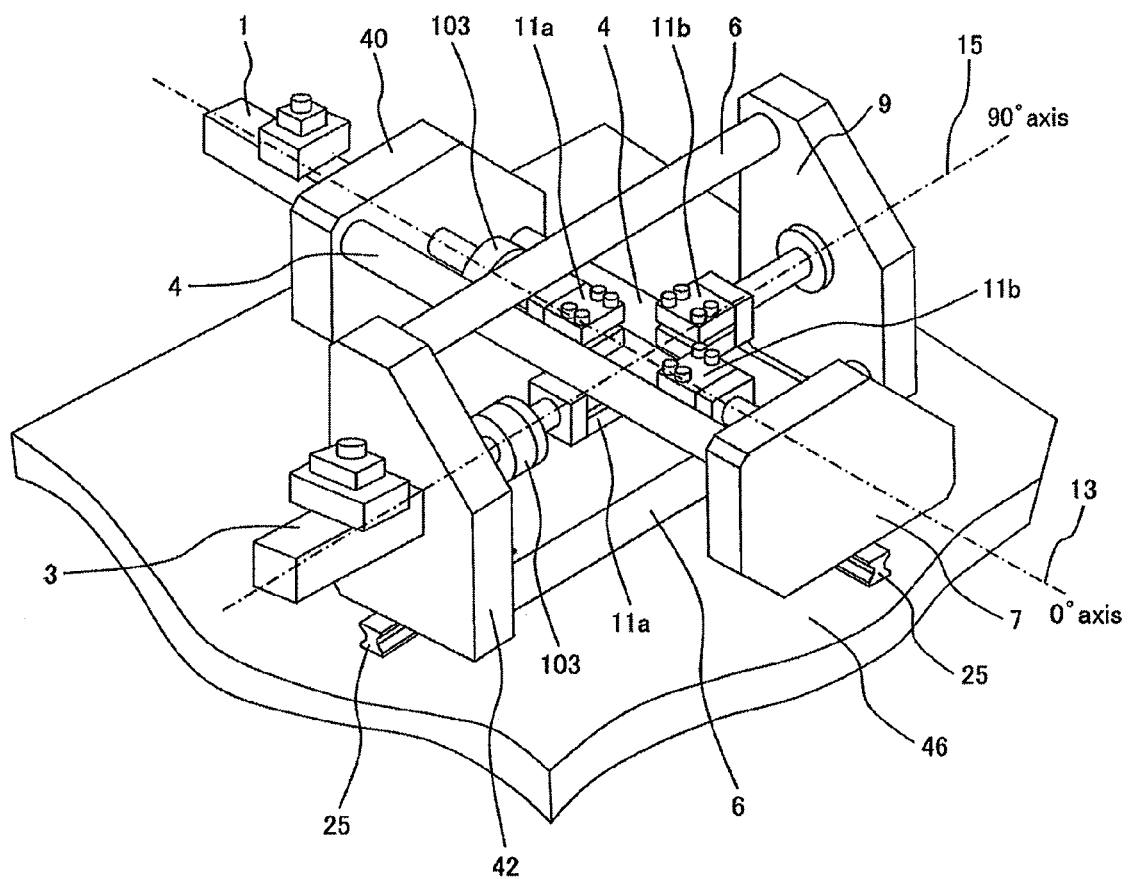
FIG. 20 is a block diagram for showing an example of the structure of the strength testing apparatus according to a fourth embodiment.
Figure 21:
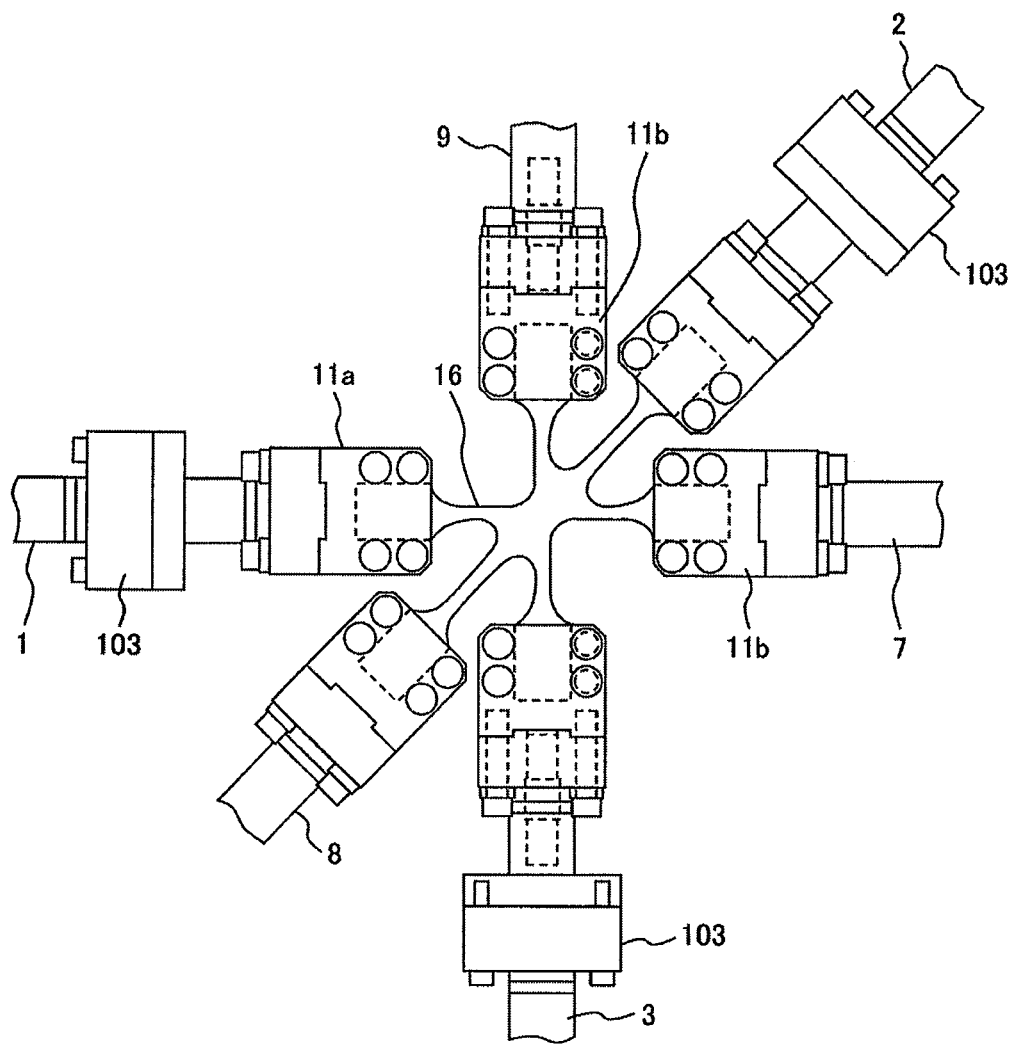
FIG. 21 is a partial enlarged view for showing another example of the structure of the strength testing apparatus according to the fourth embodiment.

If showing only the main constituent elements of the example of structure shown in FIG. 20 in the manner of a block diagram, it comes to be such figure as shown in FIG. 19. In FIG. 19, the bases 4 and 6 are depicted in the plate-like shapes thereof; however, if understanding those to be the rod-like bases, the example of structure shown in FIG. 20 is same to that shown in FIG. 19, in relation to the angular relationship of each 1-axis structure element and the direction of movement thereof. In this manner, i.e., with the structure of adopting the rod-like base, as is shown in FIG. 20, and arranging the linear guides on the actuator fixing bases and the reaction bases, it is possible to achieve the functions/effects, being same to that of the first through the third embodiment (FIGS. 11, 12, 13, 16, 17, 18 and 19). Namely, in such example of structure as shown in FIG. 20, there is shown the 2-axes structure having the testing structure of 0°-axis and the testing structure of 90°-axis; however, the present invention should not be restricted only to this, but may have a 3-axes structure, arranging those along with the 0°-axis, 90°-axis and 45°-axis, for example. In FIG. 21 is shown the structure of the plane view, in particular, of an enlarged part thereof, centering round the test piece 16, in case of modifying the strength testing apparatus according to the fourth embodiment mentioned above, into such 3-axes structure as mentioned above. In this fourth embodiment, since the rod-like bases can be disposed on both sides different from, on a boundary of the plane including all of the testing axes, it is possible to prevent the test piece from being bent outside of the surface thereof, effectively, comparing to the application of the rigidity assistance members shown in FIGS. 9 and 10.

However, the embodiments mentioned above are explained in the details thereof, for easy understanding of the present invention, and therefore, the present invention should not be restricted to those embodiments mentioned above; but may includes various variations thereof, and for example, it should not be limited, necessarily, only to that having all of the constituent elements explained in the above. Also, it is possible to add the constituent element (s) of other embodiment(s) to the constituent elements of a certain embodiment. Further, to/from/for a part of the constituent elements of each embodiment can be added/deleted/substituted other constituent element(s).

What is claimed is:

1. A testing apparatus, comprising:
a plurality of 1-axis testing structures, each 1-axis testing structure comprising:
an actuator, which is configured to move linearly, thereby to apply a load onto a test body;
an actuator fixing base, which is configured to fix said actuator at a predetermined position;
a reaction base comprising a first chucking tool, which first chucking tool is configured to chuck the test body in cooperation with a second chucking tool, which second chucking tool is provided at an end portion of said actuator; and
a base, on which said actuator fixing base and said reaction base are mounted,
wherein an axis of each of the plurality of 1-axis testing structures essentially passes through an axial center of each actuator, respectively, wherein axes of the plurality of 1-axis testing structures cross at one point, and wherein said plurality of 1-axis testing structures are arranged so that the axes of the plurality of 1-axis testing structures are included in a same plane, and
wherein said base of said one of said plurality of 1-axis testing structures is movable with respect to bases of other ones of the plurality of 1-axis testing structures.

2. The testing apparatus according to claim 1, wherein
under a condition that the test piece is not attached, the base of said one of said plurality of 1-axis testing structures that is configured to move is not prevented from moving by another 1-axis testing structure.

3. The testing apparatus according to claim 1, wherein said plurality of 1-axis testing structures includes a first 1-axis testing structure, a second 1-axis testing structure, and a third 1-axis testing structure, and the respective axes of each of the three 1-axis testing structures are arranged having a relationship such that the axis of the second 1-axis testing structure is offset by 90° from the axis of the first 1-axis testing structure, and the axis of the third 1-axis testing structure is offset by 45° from the axis of the first 1-axis testing structure.

4. The testing apparatus according to claim 1, wherein the actuator fixing base and the reaction base are connected by the base and a rigidity assistant member.

5. The testing apparatus according to claim 4, wherein the rigidity assistant member includes two or more rod members that connect the actuator fixing base and the reaction base, and each rod of the two or more rod members are in a different plane that is parallel to the plane that includes each of the axes of each of the plurality of 1-axis testing structures.

* * * * *